(12) United States Patent
Liska et al.

(10) Patent No.: US 9,623,145 B2
(45) Date of Patent: Apr. 18, 2017

(54) THIOL-ENE POLYMERIZATION WITH VINYLESTERS AND VINYLCARBONATE

(71) Applicants: Depuy Synthes Products, Inc., Raynham, MA (US); Technische Universitaet Wien, Vienna (AT)

(72) Inventors: Robert Liska, Schleinbach (AT); Xiaohua Qin, Vienna (AT); Andreas Mautner, Vienna (AT)

(73) Assignees: DePuy Synthes Products, Inc., Raynham, MA (US); Technische Universitaet Wien, Vienna (AT)

( * ) Notice: Subject to any disclaimer, the term of this patent is extended or adjusted under 35 U.S.C. 154(b) by 715 days.

(21) Appl. No.: 13/627,399

(22) Filed: Sep. 26, 2012

(65) Prior Publication Data

US 2013/0084543 A1 Apr. 4, 2013

Related U.S. Application Data

(60) Provisional application No. 61/542,522, filed on Oct. 3, 2011.

(51) Int. Cl.
| | |
|---|---|
| C08F 18/04 | (2006.01) |
| A61L 27/16 | (2006.01) |
| C08L 33/06 | (2006.01) |
| A61L 27/54 | (2006.01) |

(52) U.S. Cl.
CPC .............. *A61L 27/16* (2013.01); *A61L 27/54* (2013.01); *C08L 33/06* (2013.01); *A61L 2430/02* (2013.01)

(58) Field of Classification Search
CPC .................................................... C08L 33/06
See application file for complete search history.

(56) References Cited

U.S. PATENT DOCUMENTS

| | | | | |
|---|---|---|---|---|
| 5,100,929 | A | * | 3/1992 | Jochum et al. ............... 522/64 |
| 5,945,464 | A | * | 8/1999 | Takushima et al. .......... 522/180 |
| 6,624,211 | B2 | | 9/2003 | Karim et al. |
| 8,999,323 | B2 | * | 4/2015 | Liska et al. ............... 424/130.1 |
| 2010/0219546 | A1 | * | 9/2010 | Puttler et al. .................. 264/16 |
| 2010/0303804 | A1 | | 12/2010 | Liska et al. |
| 2010/0304338 | A1 | | 12/2010 | Cramer et al. |
| 2011/0060446 | A1 | * | 3/2011 | Ono et al. ..................... 700/119 |

FOREIGN PATENT DOCUMENTS

| | | | |
|---|---|---|---|
| GB | 1312530 A | 4/1973 | |
| WO | 97/35916 | 10/1997 | |
| WO | 2005086911 A2 | 9/2005 | |
| WO | WO 2009065162 A2 * | 5/2009 | ............. A61L 27/56 |
| WO | 2009132070 A2 | 10/2009 | |
| WO | 2013052328 | 4/2013 | |

OTHER PUBLICATIONS

PCT International Preliminary Report on Patentability from International Application No. PCT/US2012/057295 (Apr. 17, 2014).
International Search Report for International Patent Application No. PCT/US2012/0517295, dated Jan. 11, 2013, 6 pages.
Written Opinion for International Patent Application No. PCT/US2012/0517295, dated Jan. 11, 2013, 7 pages.
Chinese Office Action for Chinese Patent Application No. 201280049691.3, dated May 22, 2015, 12 pages.
Lee et al., Synthesis and Photopolymerization of Novel Multifunctional Vinyl Esters, Journal of Polymer Science: Part A: Polymer Chemistry, vol. 42, pp. 4424-4436 (2004).
Baudis et al., Methacrylate-Based Photoelastomers as Tailored Biomaterials for Artificial Vascular Grafts, Journal of Polymer Science: Part A: Polymer Chemistry, vol. 47, pp. 2664-2676 (2009).
Olofson et al., A Regiospecific and Stereospecific Route to ENOL Carbonates and Carbamates: Closer Look at a "Naked Action", Tetrahedron Letters, 1980, 21, pp. 819-822.
Olofson et al., "Simple One-Step Preparations of Vinylic Carbonates from Aldehydes", The Journal of Organic Chemistry, Jan. 1990, 55(1), 3 pages.
Rege et al., "Chemoenzymatic Synthesis and High-Throughput Screening of an Aminoglyoside-Polyamine Library: Identification of High-Affinity Displacers and DNA-Binding Ligands", J. Am. Chem. Soc., Jan. 2004, 126 pp. 12306-12315.

* cited by examiner

*Primary Examiner* — Michael Pepitone
(74) *Attorney, Agent, or Firm* — Morgan, Lewis & Bockius, LLP

(57) ABSTRACT

The present disclosure is directed, in part, to a curable composition, a method for augmenting a structure in a patient with a resorbable biocompatible polymer, and a biodegradable, resorbable implant comprising a biocompatible copolymer. An exemplary embodiment of the curable composition comprises (a) 60 wt. % to 95 wt. % of one or more vinyl ester monomers and/or vinylcarbonate monomers, wherein said one or more vinyl ester monomers and/or vinylcarbonate monomers are respectively selected from compounds of the general formulas (I) and (II) below:

$$\left[ \diagup\!\!\!\diagdown\!\!\!{\rm O}\!\!-\!\!\underset{\underset{\rm O}{\|}}{\rm C}\!\right]_n\!\!-\!\!R^1 \quad (I)$$

$$\left[ \diagup\!\!\!\diagdown\!\!\!{\rm O}\!\!-\!\!\underset{\underset{\rm O}{\|}}{\rm C}\!\!-\!\!{\rm O}\right]_m\!\!-\!\!R^2 \quad (II)$$

wherein n, m $R^1$ and $R^2$ have the meaning defined herein; (b) 0.1 to 40 wt. % of one or more multifunctional thiols; and (c) 0 to 10 wt. % of a biocompatible polymerization initiator.

15 Claims, 8 Drawing Sheets

THIOL-ENE POLYMERIZATION WITH VINYLESTERS AND VINYLCARBONATE

CROSS REFERENCE TO RELATED APPLICATION

This application claims benefit of priority from U.S. Provisional Patent Application No. 61/542,522, filed 3 Oct. 2011, all of which are incorporated by reference herein by in its entirety.

FIELD OF THE INVENTION

The present disclosure is directed, in part, to a curable composition, a method for augmenting a structure in a patient with a resorbable biocompatible polymer and a biodegradable, resorbable implant comprising a biocompatible copolymer.

BACKGROUND OF THE INVENTION

Traditional photopolymers based on acrylates and methacrylates have limited utility in biomedical applications, for example, as bone replacement materials, and dental fillers. This is due, in part, to their cytotoxicity and suboptimal mechanical properties, including low impact resistance.

Existing bone replacement materials include autografts and allografts, which consist of tissue obtained from the same or another subject of the same species. While these materials are commonly used for tissue repair and substitution, they have some serious disadvantages, such as limited availability and the possibility of donor site morbidity in the case of autografts and complications, such as viral transmission and immunogenicity in the case of allografts.

To overcome these drawbacks new synthetic biocompatible and biodegradable materials are needed. Also, since the defects to be repaired often differ in size, shape, and/or location in the body, it is necessary to develop compositions and techniques that allow the fabrication of a replacement material in any conceivable shape.

To enable proper healing and rebuilding of a bone, e.g. after removal of a tumor, it is necessary to implant a biodegradable tissue scaffold, which perfectly fits in the hole and gives mechanical support. The scaffold material must not only be biocompatible and bioresorbable, but also support attachment and differentiation of osteogenic cells. Therefore, a need exists for synthetic material that is porous to promote the supply of nutrients and cells to the site of the replacement material.

Accordingly, a need exists for curable monomer-based compositions that can easily be introduced at a site of a structure, in a patient's body, to augment the structure with a resorbable, biocompatible polymer that is cured in vivo.

BRIEF SUMMARY OF THE INVENTION

In one embodiment, the present disclosure provides for a curable composition for the preparation of biodegradable, biocompatible, cross-linked polymers. In one embodiment, the curable composition comprising (a) 60 wt. % to 95 wt. % of one or more vinyl ester monomers and/or vinylcarbonate monomers, wherein said one or more vinyl ester monomers and/or vinylcarbonate monomers are respectively selected from compounds of the general formulas (I) and (II) below:

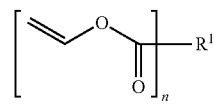

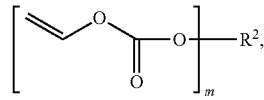

wherein n and m independently range from 2 to 1000, from 2 to 50, from 2 to 20, from 2 to 10, or from 2 to 3;

$R^1$ and $R^2$ are independently selected from the group consisting of:

(i) n-valent radicals, each of said n-valent radicals comprising a carbon chain or a carbon cycle or both, wherein said carbon chain and/or carbon cycle each, independently from one another, comprises from 1 to 30 carbon atoms, from 3 to 25 carbon atoms, from 4 to 20 carbon atoms, or from 5 to 15 carbon atoms, wherein said carbon chain can be straight, branched, saturated or unsaturated, and optionally containing one or more interspersed heteroatoms, said heteroatoms being selected from the group consisting of oxygen, sulfur and nitrogen, and/or wherein said carbon chain optionally being substituted with one or more substituents selected from the group consisting of —OH, —COOH, —CN, —CHO, and =O, wherein said carbon cycle can be saturated or unsaturated, and optionally containing one or more interspersed heteroatoms, said heteroatoms being selected from the group consisting of oxygen, sulfur and nitrogen, and/or wherein said carbon cycle optionally being substituted with one or more substituents selected from the group consisting of —OH, —COOH, —CN, —CHO, and =O, and (ii) n-valent radicals of biodegradable, biocompatible oligomers and polymers, said oligomers and polymers being selected from the group consisting of polysaccharides, polypeptides, polyamides, polyesters, polycarbonates, polyethers, and fatty acid derivatives;

(b) 0.1 to 40 wt. % of one or more multifunctional thiols; and (c) 0 to 10 wt. % of a biocompatible photo-polymerization initiator.

In an embodiment of the curable composition at least one vinyl ester monomer or vinylcarbonate monomer of the general formulas (I) or (II), accounts for 50 mole percent of all monomers contained. In another embodiment of the curable composition at least 35, preferably at least 50, mole percent of all vinyl ester monomers are difunctional, cross linking monomers in which n=2. In another embodiment of the curable composition, said one or more vinyl ester monomers and/or vinylcarbonate monomers are selected from the group consisting of adipic acid divinyl ester (AVE); octanedioic acid divinyl ester (KVE); sebacic acid divinyl ester (SEVE); diethylene glycol bis[O—(O'-vinylmaleinoyl)-polylactate] (DVMPL); trimeric fatty acid trivinyl ester (TFVE); ω, ω'-3,6,9-trioxaundecanedioic acid divinyl ester (TUVE); ethylene glycol bis(vinyl carbonate) (EGDVC); 1,4-butanediol bis(vinyl carbonate) (BDDVC); 1,6-hexanediol bis(vinyl carbonate) (HDDVC); glycerine tris(vinyl carbonate) (GTVC); diethylene glycol bis(vinyl carbonate) (DEGDVC); polyethylene glycol (400) bis(vinyl carbonate) (PEGDVC); ricinus oil tris(vinyl carbonate) (RiTVC); hydrated ricinus oil tris(vinyl carbonate) (HRiTVC); and diethylene glycol bis[O—(O'-vinyloxycarbonyl) polylactate] (DEG(PLAVC)$_2$). In an embodiment, said one or more vinyl ester monomers are selected from the group consisting of adipic acid divinyl ester (AVE); octanedioic acid divinyl ester (KVE); sebacic acid divinyl ester (SEVE); diethylene glycol bis[O—(O'-vinylmaleinoyl)-polylactate]) (DVMPL); trimeric fatty acid trivinyl ester (TFVE); and ω, ω'-3,6,9-trioxaundecanedioic acid divinyl ester (TUVE).

In another embodiment, $R^2$ is derived from one or more diols, said one or more diols being selected from the group consisting of: 1,3-propanediol, 1,4-butanediol, 1,5-pentanediol, 1,6-hexanediol, 1,7-heptanediol, 1,8-octanediol, 1,9-nonanediol, 1,10-decanediol, and 1,12-dodecanediol. In another embodiment, $R^2$ is derived from one or more diols, said one or more diols comprising a polyethylene glycol or a polypropylene glycol. In another embodiment, said polyethylene glycol has a molecular weight ranging from 200 g/mole to 1000 g/mole. In another embodiment, said one or more vinyl carbonate monomers are selected from the group consisting of ethylene glycol bis(vinyl carbonate) (EGDVC); 1,4-butanediol bis(vinyl carbonate) (BDDVC); 1,6-hexanediol bis(vinyl carbonate) (HDDVC); glycerine tris(vinyl carbonate) (GTVC); diethylene glycol bis(vinyl carbonate) (DEGDVC); polyethylene glycol(400) bis(vinyl carbonate) (PEGDVC); and ricinus oil tris(vinyl carbonate) (RiTVC).

In an embodiment, said one or more multifunctional thiols are selected from the group consisting of: pentaerythritol tetra-(3-mercaptopropionate), ethoxylated pentaerythritol tetra-(3-mercaptopropionate), trimethylpropane tri(3-mercapto-propionate) and ethoxylated trimethylpropane tri(3-mercapto-propionate).

Another aspect of the present disclosure provides for a method for augmenting a structure in a patient, said method comprising implanting a composition in accordance with the present invention into said patient at a site of the structure and initiating said liquid/viscous composition to thereby form a solid resorbable, biocompatible polymer. In an embodiment, said initiating is performed by irradiating said curable composition at the site of the structure. In another embodiment, the implanting step is performed by injecting a composition in accordance with the present invention through a hole in the patient's skin and into a vertebra. In another embodiment, the implanting step is performed by (a) inserting a balloon through a hole in the patient's skin into a vertebra; (b) inflating the balloon to create a void at the site of the structure; and (c) injecting a composition in accordance with the present invention through a hole in the patient's skin into a vertebra.

In another embodiment, the implanting step is performed by injecting the composition of the present invention into the patient's oral and maxillofacial region. In another embodiment, the structure is located at a site selected from the group consisting of a fracture, a deformity, a tumor and combinations thereof.

Another aspect of the present disclosure provides for a biodegradable implant, said biodegradable implant comprising a copolymer having monomer units of (a) 60 wt. % to 95 wt. % of one or more vinyl ester monomers and/or vinyl-carbonate monomers, wherein said one or more vinyl ester monomers and/or vinylcarbonate monomers are respectively selected from compounds of the general formulas (I) and (II) below:

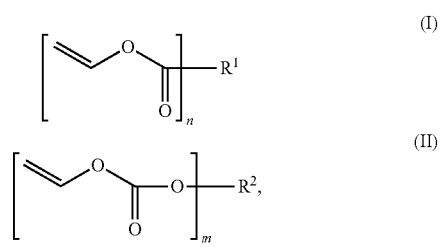

wherein n, m, $R^1$ and $R^2$ have the above-stated definitions.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention can be embodied in different forms and thus should not be construed as being limited to the embodiments set forth herein.

DETAILED DESCRIPTION OF THE INVENTION

Figure 1:
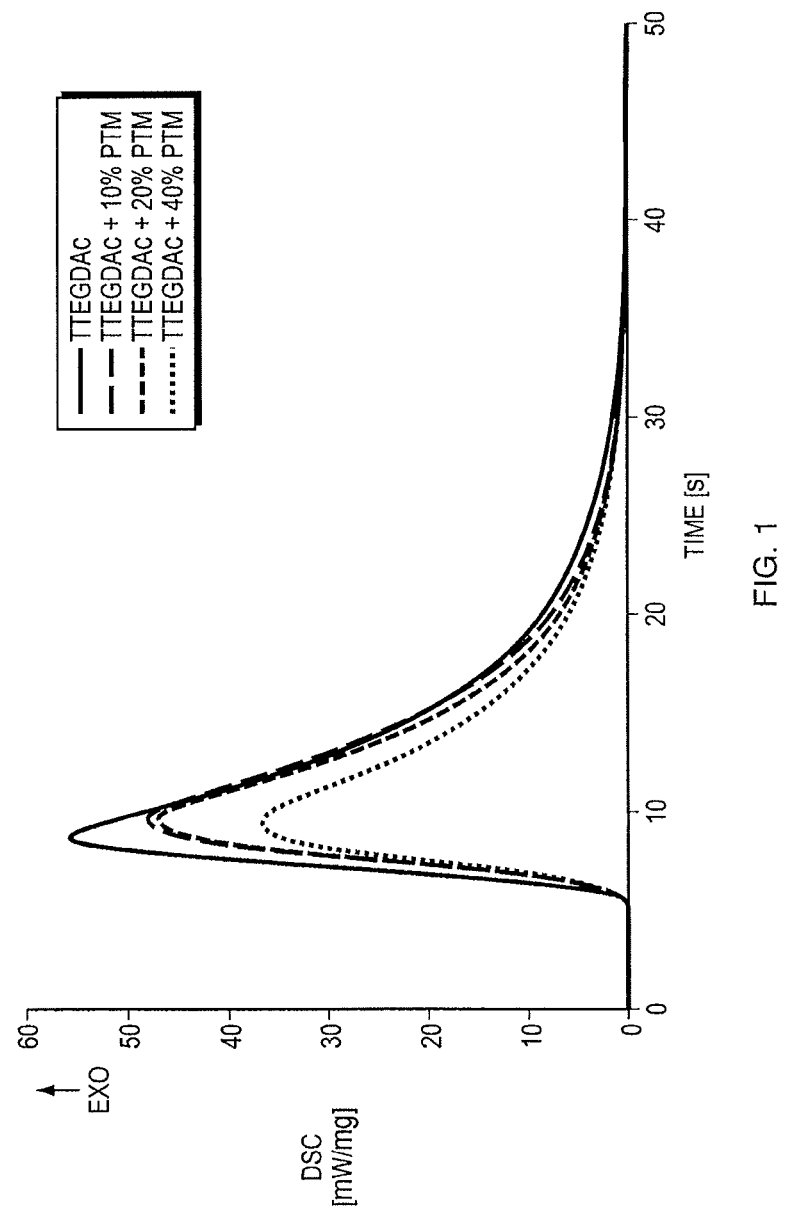
FIG. 1 illustrates photo-DSC measurements of TTEGDAc containing different amounts of the thiol pentaerythritol tetra(3-mercaptopropionate) (PTM)

The present subject matter will now be described more fully hereinafter with reference to the accompanying Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entirety.

A. Compositions

In one embodiment, the present disclosure provides for a curable composition for the preparation of biodegradable, biocompatible, cross linked polymers. In one embodiment, a curable composition comprises (a) 60 wt. % to 95 wt. % of one or more vinyl ester monomers and/or vinylcarbonate monomers, wherein said one or more vinyl ester monomers and/or vinylcarbonate monomers are respectively selected from compounds of the general formulas (I) and (II) below:

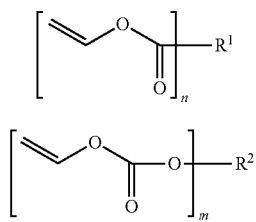

wherein n and m independently range from 2 to 1000, from 2 to 50, from 2 to 20, from 2 to 10, or from 2 to 3;

$R^1$ and $R^2$ are independently selected from the group consisting of:
  (i) n-valent radicals, each of said n-valent radicals comprising a carbon chain or a carbon cycle or both,
  wherein said carbon chain and/or carbon cycle each, independently from one another, comprises from 1 to 30 carbon atoms, from 3 to 25 carbon atoms, from 4 to 20 carbon atoms, or from 5 to 15 carbon atoms,
  wherein said carbon chain can be straight, branched, saturated or unsaturated, and optionally containing one or more interspersed heteroatoms, said heteroatoms being selected from the group consisting of oxygen, sulfur and nitrogen, and/or
  wherein said carbon chain optionally being substituted with one or more substituents selected from the group consisting of —OH, —COOH, —CN, —CHO, and =O,
  wherein said carbon cycle can be saturated or unsaturated, and optionally containing one or more interspersed heteroatoms, said heteroatoms being selected from the group consisting of oxygen, sulfur and nitrogen, and/or
  wherein said carbon cycle optionally being substituted with one or more substituents selected from the group consisting of —OH, —COOH, —CN, —CHO, and =O, and
  (ii) n-valent radicals of biodegradable, biocompatible oligomers and polymers, said oligomers and polymers being selected from the group consisting of polysaccharides, polypeptides, polyamides, polyesters, polycarbonates, polyethers, and fatty acid derivatives;

(b) 0.1 to 40 wt. % of one or more multifunctional thiols; and (c) 0 to 10 wt. % of a biocompatible photo-polymerization initiator.

As shown in the compounds of the general Formulas (I) and (II) above, several vinyl ester moieties and several vinyl carbonate moieties may be bound to the groups $R^1$ and $R^2$, respectively. The number of vinyl ester moieties (n) or the number of vinyl carbonate moieties (m) in the composition is determined by the appropriate choice of the parameters n and m. If vinyl esters or vinyl carbonates of biopolymers with high molecular weights, for example of over 10,000 or even over 1,000,000 g/mol, are used, for example, if starch is used as a biopolymer, up to 1,000 reactive sites, i.e. vinyl ester groups, may be present on the polymer backbone, depending on the degree of substitution. However, due to the high cross linking density, which may be too high for some applications, as well as in order to increase the dissolution rates of the polymers in the body, fewer reactive sites, i.e. up to 50, up to 20, or up to 10 vinyl ester groups, per monomer molecule are generally preferred as groups $R^1$ and $R^2$ in the case of biopolymers. Especially if not biopolymers but monomers or short-chain oligomers (such as dimers) are used as $R^1$ and $R^2$, preferably up to 10 vinyl ester or vinyl carbonate groups, more preferably up to 3 vinyl ester or vinyl carbonate groups are present in the monomer molecule.

Vinyl ester monomers of formula (I) are preferably selected from aliphatic carboxylic acids and hydroxy carboxylic acids with 4 to 20 carbon atoms, sugar acids, amino acids as well as polymers and co-polymers of the above-mentioned acids, more preferably from the following acids and their derivatives: succinic acid, adipic acid, fumaric acid, citric acid, tartaric acid, aspartic acid, oxoglutaric acid, glutaminic acid, galactaric acid, ethylenediaminetetraacetic acid, butanetetracarboxylic acid, cyclo-pentanetetracarboxylic acid, polyglutamic acid, polyaspartic acid, hyaluronic acid, polylactic acid, polyglycolic acid, and poly(lactide-co-glycolide).

If $R^2$ is derived from the residue of a biopolymer, said biopolymer may, for example, be selected from polyethylene glycol, gelatine, chitosan, cellulose, amylose, and glycogen. This choice ensures that the degradation products of a polymer prepared from the composition are well tolerated or that the starting substances for the composition are readily available.

The choice of the number of carbon atoms of the groups $R^1$ and $R^2$ depends, inter alia, on the respective values of n and m. Although compounds having very short chains as well as long-chained radicals with up to 30 carbon atoms, being strongly branched or interrupted by cyclic structures, may be used, such very short-chained, very long-chained, or highly branched structures may not be suitable for some applications. For example, compounds having a very low molecular weight tend to be difficult to handle due to their relative volatility, whereas long-chained or highly branched groups tend be more difficult to decompose within the body. Thus, there may be tradeoffs involved in the choice of the number of carbon atoms of the groups $R^1$ and $R^2$. Accordingly, in an embodiment of the present invention, each of $R^1$ and $R^2$ preferably has from 3 carbon atoms to 25, from 4 carbon atoms to 20 carbon atoms, or from 5 carbon atoms to 15 carbon atoms.

The groups $R^1$ and $R^2$ may optionally contain interspersed heteroatoms due to the fact that biological molecules with the specified chain lengths such as in sugar (acid), amino acid or peptide or fatty acid radicals, from which the vinyl ester and vinyl carbonate monomers of the present invention are prepared, often contain heteroatoms. The groups $R^1$ and $R^2$ may also be optionally substituted or may contain unsaturation and/or branching sites. The optional substituents may also serve to promote the adherence of cells to the surface of the polymer product prepared from the composition of the present invention.

The compositions of the present invention may contain one vinyl ester monomer of formula (I) or one vinyl carbonate monomer of the formula (II), said vinyl ester monomer or vinyl carbonate monomer being at least bifunctional, i.e. a divinyl ester or divinyl carbonate, in order to yield the required minimum cross linking density upon polymerization. In some embodiments, the compositions preferably contain several different vinyl ester monomers and/or vinylcarbonate monomers, e.g. bifunctional and/or higher functional monomers, to facilitate control of the degree of cross linking produced via curing of the compositions. In some embodiments, the composition comprises different vinyl ester monomers corresponding to the compounds of the formula (I). In some embodiments, the composition comprises different vinyl carbonate monomers corresponding to the compounds of the formula (II). In other embodiments, the composition comprises at least one vinyl ester monomer corresponding to the compounds of the formula (I) and at least one vinyl carbonate monomer corresponding to the compounds of the formula (II). Thus, the compositions of the present invention may contain, for example, combinations of several different vinyl esters and/or several different vinyl carbonates. The choice of such combinations is not specifically limited and may be selected freely depending on the respective application of the polymer which is to be prepared therefrom, as long as the desired properties of the cured product are obtained in the course of the polymerization.

In an embodiment, at least one vinyl ester monomer accounts for at least 50 mole percent of all monomers contained in the composition. In another embodiment, at least one vinyl ester monomer accounts for at least 70 mole percent of all monomers contained in the composition. In another embodiment, at least one vinyl ester monomer accounts for at least 90 mole percent of all monomers contained in the composition. In an embodiment, at least one vinyl ester monomer accounts for at least 50 mole percent to 90 mole percent of all monomers contained in the composition. In another embodiment, at least one vinyl ester monomer accounts for at least 50 mole percent to 85 mole percent of all monomers contained in the composition. In an embodiment, at least one vinyl ester monomer accounts for at least 50 mole percent to 80 mole percent of all monomers contained in the composition. In an embodiment, at least one vinyl ester monomer accounts for at least 50 mole percent to 75 mole percent of all monomers contained in the composition. In another embodiment, at least one vinyl ester monomer accounts for at least 50 mole percent to 70 mole percent of all monomers contained in the composition. In another embodiment, at least one vinyl ester monomer accounts for at least 50 mole percent to 65 mole percent of all monomers contained in the composition. In an embodiment, at least one vinyl ester monomer accounts for at least 50 mole percent to 60 mole percent of all monomers contained in the composition.

In an embodiment, at least one vinyl ester monomer accounts for at least 35 mole percent to 50 mole percent of all monomers contained in the composition. In an embodiment, at least one vinyl ester monomer accounts for at least 35 mole percent to 47 mole percent of all monomers contained in the composition. In an embodiment, at least one vinyl ester monomer accounts for at least 35 mole percent to 45 mole percent of all monomers contained in the composition. In an embodiment, at least one vinyl ester monomer accounts for at least 35 mole percent to 43 mole percent of all monomers contained in the composition. In an embodiment, at least one vinyl ester monomer accounts for at least 35 mole percent to 41 mole percent of all monomers contained in the composition. In an embodiment, at least one vinyl ester monomer accounts for at least 35 mole percent to 39 mole percent of all monomers contained in the composition. In an embodiment, at least one vinyl ester monomer accounts for at least 35 mole percent to 37 mole percent of all monomers contained in the composition.

In an embodiment, at least one vinyl carbonate monomer accounts for at least 50 mole percent of all monomers contained in the composition. In another embodiment, at least one vinyl carbonate monomer accounts for at least 70 mole percent of all monomers contained in the composition. In another embodiment, at least one vinyl carbonate monomer accounts for at least 90 mole percent of all monomers contained in the composition. In an embodiment, at least one vinyl carbonate monomer accounts for at least 50 mole percent to 90 mole percent of all monomers contained in the composition. In another embodiment, at least one vinyl carbonate monomer accounts for at least 50 mole percent to 85 mole percent of all monomers contained in the composition. In an embodiment, at least one vinyl carbonate monomer accounts for at least 50 mole percent to 80 mole percent of all monomers contained in the composition. In an embodiment, at least one vinyl carbonate monomer accounts for at least 50 mole percent to 75 mole percent of all monomers contained in the composition. In another embodiment, at least one vinyl carbonate monomer accounts for at least 50 mole percent to 70 mole percent of all monomers contained in the composition. In another embodiment, at least one vinyl carbonate monomer accounts for at least 50 mole percent to 65 mole percent of all monomers contained in the composition. In an embodiment, at least one vinyl carbonate monomer accounts for at least 50 mole percent to 60 mole percent of all monomers contained in the composition.

In an embodiment, at least one vinyl carbonate monomer accounts for at least 35 mole percent to 50 mole percent of all monomers contained in the composition. In an embodiment, at least one vinyl carbonate monomer accounts for at least 35 mole percent to 47 mole percent of all monomers contained in the composition. In an embodiment, at least one vinyl carbonate monomer accounts for at least 35 mole percent to 45 mole percent of all monomers contained in the composition. In an embodiment, at least one vinyl carbonate monomer accounts for at least 35 mole percent to 43 mole percent of all monomers contained in the composition. In an embodiment, at least one vinyl carbonate monomer accounts for at least 35 mole percent to 41 mole percent of all monomers contained in the composition. In an embodiment, at least one vinyl carbonate monomer accounts for at least 35 mole percent to 39 mole percent of all monomers contained in the composition. In an embodiment, at least one vinyl carbonate monomer accounts for at least 35 mole percent to 37 mole percent of all monomers contained in the composition.

The vinyl ester and vinyl carbonate monomers of the present compositions are either commercially available or may be prepared according to procedures known from literature or according to the procedures disclosed in the Examples section of the present disclosure. Those skilled in the art will understand that the reaction parameters may have to be changed correspondingly in order to synthesize further compounds not described herein but which still full within the scope of the present disclosure. Carbonates suitable for use in the present invention may be prepared in accordance with the procedures detailed in the following literature references, all of which are incorporated herein in their entirety: R. A. Olofson and J. Cuomo, Tetrahedron Lett. 21(9), 819-22 (1980), describe the synthesis of isobutyl vinyl carbonate from trimethylsilyl vinyl ether and chlorofumaric acid isobutylester using benzyltrimethylammonium fluoride as a catalyst; R. A. Olofson, Dang Vu Anh; D. S. Morrison, and P. F. De Cusati, J. Org. Chem. 55(1), 1-3 (1990), describe a one-step synthesis from chloro- or fluorofumaric acid esters and aldehyds using crown ether catalysis; and K. Rege, S. Hu, J. A. Moore, J. S. Dordick, and S. M. Cramer, J. Am. Chem. Soc. 126(39), 12306-12315 (2004), describe the chemoenzymatic and thus regioselective synthesis starting from methyleneoxime vinyl carbonate and alcohols.

Non-limiting examples of possible precursor substances for the preparation of vinyl carbonate monomers include various mono- and polyalcohols, including sugar and sugar acid derivatives, e.g. various glycols, glycerine, hexanediol, trimethylol propane, stearyl tartrate, glucose, ribose, fructose, glycerine aldehyde, dihydroxyacetone, deoxyribose, cellobiose, glucopyranose, erythrose, threose, as well as their thio-analogues, polymers and biopolymers, e.g. starch, cellulose, chitosan, alginate, hydroxyethyl celluose, hydroxyethyl starch, hyaluronate, gelatine, casein, polyvinyl alcohol, poly(ethylene carbonate), poly(1,2-propylene carbonate), polycaprolactonediol, but also two- and three-block-co-polymers such as PEG-caprolactone, PEG-glycols, PEG-lactides, PEG-ethylene carbonate, and PEG-propylene carbonate, as well as different compounds showing biological activities such as salicylic acid ethyl ester, ascorbinic acid, ubiquinone, gallic acid, citric acid, curcumin, retinol, calciferol, thiamine, diaminopyrimidine, 1,3-propanediol, 1,4-butanediol, 1, 5-pentanediol, 1,6-hexanediol, 1,7-heptanediol, 1,8-octanediol, 1,9-nonanediol, 1,10-decanediol, and 1,12-dodecanediol.

A.1 Initiators

The compositions of the present invention may contain one or more polymerization initiators. Radical polymerization of the compositions may be initiated in a variety of different ways as follows. Radical polymerization of the composition of the present invention may be initiated by any suitable free-radical initiators including photoinitiators, thermally activated initiators, redox initiator systems, ionic initiators or combinations thereof. Accordingly, in an embodiment a set of one or more photoinitiators is used to initiate the radical polymerization. In another embodiment, a set of one or more redox initiator systems is used to initiate the radical polymerization. In yet another embodiment, a set of one or more thermal initiators is used to initiate the radical polymerization. In another embodiment, a set of one or more photoinitiators is used in combination with one or more redox initiator systems. In another embodiment, a set one or more thermal initiators is used in combination with one or more redox initiator systems. In another embodiment, a set of one or more photoinitiators is used in combination with a set of one or more thermal initiators. In yet another embodiment, a set of one or more photoinitiators and one or more thermal initiators are used in combination with one or more redox initiator systems.

One of ordinary skill in the art would appreciate that the choice of the concentration of the radical polymerization initiator to be used may be adjusted depending on a number of factors, including the type of the initiator, whether the initiator is used alone or in combination with other initiators, the desirable rate of curing, and how the material is applied. In an embodiment, the concentration of the initiator is between about 0.0% (w/w) to about 10% (w/w) of the polymerizable composition.

In an embodiment, the concentration of the initiator is selected from the group consisting of 0.05% (w/w) of the polymerizable composition, about 0.1% (w/w) of the polymerizable composition, about 0.15% (w/w) of the polymerizable composition, about 0.2% (w/w) of the polymerizable composition, about 0.25% (w/w) of the polymerizable composition, about 0.3% (w/w) of the polymerizable composition, about 0.35% (w/w) of the polymerizable composition, about 0.4% (w/w) of the polymerizable composition, about 0.45% (w/w) of the polymerizable composition, about 0.5% (w/w) of the polymerizable composition, about 0.55% (w/w) of the polymerizable composition, about 0.6% (w/w) of the polymerizable composition, about 0.65% (w/w) of the polymerizable composition, about 0.7% (w/w) of the polymerizable composition, about 0.75% (w/w) of the polymerizable composition, about 0.8% (w/w) of the polymerizable composition, about 0.85% (w/w) of the polymerizable composition, about 0.9% (w/w) of the polymerizable composition, about 0.95% (w/w) of the polymerizable composition, about 1% (w/w) of the polymerizable composition, about 1.05% (w/w) of the polymerizable composition, about 1.1% (w/w) of the polymerizable composition, about 1.15% (w/w) of the polymerizable composition, about 1.2% (w/w) of the polymerizable composition, about 1.25% (w/w) of the polymerizable composition, about 1.3% (w/w) of the polymerizable composition, about 1.35% (w/w) of the polymerizable composition, about 1.4% (w/w) of the polymerizable composition, about 1.45% (w/w) of the polymerizable composition, about 1.5% (w/w) of the polymerizable composition, about 1.55% (w/w) of the polymerizable composition, about 1.6% (w/w) of the polymerizable composition, about 1.65% (w/w) of the polymerizable composition, about 1.7% (w/w) of the polymerizable composition, about 1.75% (w/w) of the polymerizable composition, about 1.8% (w/w) of the polymerizable composition, about 1.85% (w/w) of the polymerizable composition, about 1.9% (w/w) of the polymerizable composition, about 1.95% (w/w) of the polymerizable composition, about 2% (w/w) of the polymerizable composition, about 2.05% (w/w) of the polymerizable composition, about 2.1% (w/w) of the polymerizable composition, about 2.15% (w/w) of the polymerizable composition, about 2.2% (w/w) of the polymerizable composition, about 2.25% (w/w) of the polymerizable composition, about 2.3% (w/w) of the polymerizable composition, about 2.35% (w/w) of the polymerizable composition, about 2.4% (w/w) of the polymerizable composition, about 2.45% (w/w) of the polymerizable composition, about 2.5% (w/w) of the polymerizable composition, about 2.55% (w/w) of the polymerizable composition, about 2.6% (w/w) of the polymerizable composition, about 2.65% (w/w) of the polymerizable composition, about 2.7% (w/w) of the polymerizable composition, about 2.75% (w/w) of the polymerizable composition, about 2.8% (w/w) of the polymerizable composition, about 2.85% (w/w) of the polymerizable composition, about 2.9% (w/w) of the polymerizable composition, about 2.95% (w/w) of the polymerizable composition, about 3% (w/w) of the polymerizable composition, about 3.05% (w/w) of the polymerizable composition, about 3.1% (w/w) of the polymerizable composition, about 3.15% (w/w) of the polymerizable composition, about 3.2% (w/w) of the polymerizable composition, about 3.25% (w/w) of the polymerizable composition, about 3.3% (w/w) of the polymerizable composition, about 3.35% (w/w) of the polymerizable composition, about 3.4% (w/w) of the polymerizable composition, about 3.45% (w/w) of the polymerizable composition, about 3.5% (w/w) of the polymerizable composition, about 3.55% (w/w) of the polymerizable composition, about 3.6% (w/w) of the polymerizable composition, about 3.65% (w/w) of the polymerizable composition, about 3.7% (w/w) of the polymerizable composition, about 3.75% (w/w) of the polymerizable composition, about 3.8% (w/w) of the polymerizable composition, about 3.85% (w/w) of the polymerizable composition, about 3.9% (w/w) of the polymerizable composition, about 3.95% (w/w) of the polymerizable composition, about 4% (w/w) of the polymerizable composition, about 4.05% (w/w) of the polymerizable composition, about 4.1% (w/w) of the polymerizable composition, about 4.15% (w/w) of the polymerizable composition, about 4.2% (w/w) of the polymerizable composition, about 4.25% (w/w) of the polymerizable composition, about 4.3% (w/w) of the polymerizable composition, about 4.35% (w/w) of the polymerizable composition, about 4.4% (w/w) of the polymerizable composition, about 4.45% (w/w) of the polymerizable composition, about 4.5% (w/w) of the polymerizable composition, about 4.55% (w/w) of the polymerizable composition, about 4.6% (w/w) of the polymerizable composition, about 4.65% (w/w) of the polymerizable composition, about 4.7% (w/w) of the polymerizable composition, about 4.75% (w/w) of the polymerizable composition, about 4.8% (w/w) of the polymerizable composition, about 4.85% (w/w) of the polymerizable composition, about 4.9% (w/w) of the polymerizable composition, about 4.95% (w/w) of the polymerizable composition, about 5% (w/w) of the polymerizable composition, about 5.05% (w/w) of the polymerizable composition, about 5.1% (w/w) of the polymerizable composition, about 5.15% (w/w) of the polymerizable composition, about 5.2% (w/w) of the polymerizable composition, about 5.25% (w/w) of the polymerizable composition, about 5.3% (w/w) of the polymerizable composition, about 5.35% (w/w) of the polymerizable composition, about 5.4% (w/w) of the polymerizable composition, about 5.45% (w/w) of the polymerizable composition, about 5.5% (w/w) of the polymerizable composition, about 5.55% (w/w) of the polymerizable composition, about 5.6% (w/w) of the polymerizable composition, about 5.65% (w/w) of the polymerizable composition, about 5.7% (w/w) of the polymerizable composition, about 5.75% (w/w) of the polymerizable composition, about 5.8% (w/w) of the polymerizable composition, about 5.85% (w/w) of the polymerizable composition, about 5.9% (w/w) of the polymerizable composition, about 5.95% (w/w) of the polymerizable composition, about 6% (w/w) of the polymerizable composition, about 6.05% (w/w) of the polymerizable composition, about 6.1% (w/w) of the polymerizable composition, about 6.15% (w/w) of the polymerizable composition, about 6.2% (w/w) of the polymerizable composition, about 6.25% (w/w) of the polymerizable composition, about 6.3% (w/w) of the polymerizable composition, about 6.35% (w/w) of the polymerizable composition, about 6.4% (w/w) of the polymerizable composition, about 6.45% (w/w) of the polymerizable composition, about 6.5% (w/w) of the polymerizable composition, about 6.55% (w/w) of the polymerizable composition, about 6.6% (w/w) of the polymerizable composition, about 6.65% (w/w) of the polymerizable composition, about 6.7% (w/w) of the polymerizable composition, about 6.75% (w/w) of the polymerizable composition, about 6.8% (w/w) of the polymerizable composition, about 6.85% (w/w) of the polymerizable composition, about 6.9% (w/w) of the polymerizable composition, about 6.95% (w/w) of the polymerizable composition, about 7% (w/w) of the polymerizable composition, about 7.05% (w/w) of the polymerizable composition, about 7.1% (w/w) of the polymerizable composition, about 7.15% (w/w) of the polymerizable composition, about 7.2% (w/w) of the polymerizable composition, about 7.25% (w/w) of the polymerizable composition, about 7.3% (w/w) of the polymerizable composition, about 7.35% (w/w) of the polymerizable composition, about 7.4% (w/w) of the polymerizable composition, about 7.45% (w/w) of the polymerizable composition, about 7.5% (w/w) of the polymerizable composition, about 7.55% (w/w) of the polymerizable composition, about 7.6% (w/w) of the polymerizable composition, about 7.65% (w/w) of the polymerizable composition, about 7.7% (w/w) of the polymerizable composition, about 7.75% (w/w) of the polymerizable composition, about 7.8% (w/w) of the polymerizable composition, about 7.85% (w/w) of the polymerizable composition, about 7.9% (w/w) of the polymerizable composition, about 7.95% (w/w) of the polymerizable composition, about 8% (w/w) of the polymerizable composition, about 8.05% (w/w) of the polymerizable composition, about 8.1% (w/w) of the polymerizable composition, about 8.15% (w/w) of the polymerizable composition, about 8.2% (w/w) of the polymerizable composition, about 8.25% (w/w) of the polymerizable composition, about 8.3% (w/w) of the polymerizable composition, about 8.35% (w/w) of the polymerizable composition, about 8.4% (w/w) of the polymerizable composition, about 8.45% (w/w) of the polymerizable composition, about 8.5% (w/w) of the polymerizable composition, about 8.55% (w/w) of the polymerizable composition, about 8.6% (w/w) of the polymerizable composition, about 8.65% (w/w) of the polymerizable composition, about 8.7% (w/w) of the polymerizable composition, about 8.75% (w/w) of the polymerizable composition, about 8.8% (w/w) of the polymerizable composition, about 8.85% (w/w) of the polymerizable composition, about 8.9% (w/w) of the polymerizable composition, about 8.95% (w/w) of the polymerizable composition, about 9% (w/w) of the polymerizable composition, about 9.05% (w/w) of the polymerizable composition, about 9.1% (w/w) of the polymerizable composition, about 9.15% (w/w) of the polymerizable composition, about 9.2% (w/w) of the polymerizable composition, about 9.25% (w/w) of the polymerizable composition, about 9.3% (w/w) of the polymerizable composition, about 9.35% (w/w) of the polymerizable composition, about 9.4% (w/w) of the polymerizable composition, about 9.45% (w/w) of the polymerizable composition, about 9.5% (w/w) of the polymerizable composition, about 9.55% (w/w) of the polymerizable composition, about 9.6% (w/w) of the polymerizable composition, about 9.65% (w/w) of the polymerizable composition, about 9.7% (w/w) of the polymerizable composition, about 9.75% (w/w) of the polymerizable composition, about 9.8% (w/w) of the polymerizable composition, about 9.85% (w/w) of the polymerizable composition, about 9.9% (w/w) of the polymerizable composition, and about 9.95% (w/w) of the polymerizable composition.

In another embodiment, the concentration of the initiator is between about 0.05% (w/w) to about 10% (w/w) of the polymerizable composition. In another embodiment, the concentration of the initiator is between about 0.05% (w/w) to about 5% (w/w) of the polymerizable composition. In another embodiment, the concentration of the initiator is between about 0.05% (w/w) to about 1% (w/w) of the polymerizable composition. In another embodiment, the concentration of the initiator is between about 0.05% (w/w) to about 2% (w/w) of the polymerizable composition. In another embodiment, the concentration of the initiator is between about 0.05% (w/w) to about 3% (w/w) of the polymerizable composition. In another embodiment, the concentration of the initiator is between about 0.05% (w/w) to about 4% (w/w) of the polymerizable composition. In another embodiment, the concentration of the initiator is between about 0.05% (w/w) to about 6% (w/w) of the polymerizable composition. In another embodiment, the concentration of the initiator is between about 0.05% (w/w) to about 7% (w/w) of the polymerizable composition. In another embodiment, the concentration of the initiator is between about 0.05% (w/w) to about 8% (w/w) of the polymerizable composition. In another embodiment, the concentration of the initiator is between about 0.05% (w/w) to about 9% (w/w) of the polymerizable composition. In yet another embodiment, the concentration of the initiator is between about 0.05% (w/w) to about 0.1% (w/w) of the polymerizable composition. In another embodiment, the concentration of the initiator is between about 0.05% (w/w) to about 0.2% (w/w) of the polymerizable composition. In another embodiment, the concentration of the initiator is between about 0.05% (w/w) to about 0.3% (w/w) of the polymerizable composition. In another embodiment, the concentration of the initiator is between about 0.05% (w/w) to about 0.4% (w/w) of the polymerizable composition. In another embodiment, the concentration of the initiator is between about 0.05% (w/w) to about 0.5% (w/w) of the polymerizable composition. In another embodiment, the concentration of the initiator is between about 0.05% (w/w) to about 0.6% (w/w) of the polymerizable composition. In another embodiment, the concentration of the initiator is between about 0.05% (w/w) to about 0.7% (w/w) of the polymerizable composition. In another embodiment, the concentration of the initiator is between about 0.05% (w/w) to about 0.8% (w/w) of the polymerizable composition. In another embodiment, the concentration of the initiator is between about 0.05% (w/w) to about 0.9% (w/w) of the polymerizable composition. In some embodiments of the photoinitiators and/or the redox initiator systems, the concentration of the initiators is preferably less than 1% (w/w) of the polymerizable composition; more preferably between 0.05 and 0.1% (w/w).

In some embodiments of thermal initiator(s), the preferred concentration range is about 0.05% (w/w) to about 2% (w/w) of the polymerizable composition.

A.1.1 Photoinitiators

A photoinitiator is an initiator activated by electromagnetic radiation. Such radiation could be ultraviolet light (e.g., long wavelength ultraviolet light), light in the visible region, focused laser light, infra-red and near-infra-red light, X-ray radiation or gamma radiation. Based on the mechanism by which initiating radicals are formed, photoinitiators are generally divided into two classes: Type I photoinitiators and Type II photoinitiators. Type I photoinitiators undergo a unimolecular bond cleavage upon irradiation to yield free radicals. Type II photoinitiators undergo a bimolecular reaction where the excited state of the photoinitiator interacts with a second molecule (a coinitiator) to generate free radicals. While UV photoinitiators of both Type I and Type II are available, visible light photoinitiators predominantly belong to the Type II class of photoinitiators. Various classes of available Type I photoinitiators include benzoin ethers, benzil ketals, α-dialkoxy-acetophenones, α-hydroxy-alkylphenones, α-amino-alkylphenones, and acyl-phosphine oxides. And various available classes of available Type II photoinitiators include benzophenones/amines, and thioxanthones/amines.

Non-limiting examples of benzophenone-based type II polymeric photoinitiators include poly(2-(4-benzophenone methylene ether)-1,3-dihydroxypropane maleate)) ("PBM"), poly(2-(4-benzophenone methylene ether)-1,3-dihydroxypropane succinate)) ("PBS"), and poly(2-(4-benzophenone methylene ether)-1,3-dihydroxypropane-co-2-(phenyl-methylene-ether)-1,3-dihydroxypropane maleate)) ("PBPM").

Other non-limiting examples of biocompatible photoinitiators include beta carotene, riboflavin, Irgacure 651® (2,2-dimethoxy-2-phenylacetophenone), phenylglycine, dyes such as eosin dye, and initiators such as 2,2-dimethyl-2-phenylacetophenone, 2-methoxy-2-phenylacetophenone, and camphorquinone.

Ultraviolet and visible sensitive photoinitiators include 2-hydroxy-1-[4-(hydroxyethoxy)phenyl]-2-methyl-1-propanone (Irgacure 2959), acylphosphine oxides (e.g., Lucirin TPO or 2,4,6,-trimethylbenzoyldiphenylphosphine oxide); and camphorquinone (CQ)/amine (dimethyl-p-toluidine, DMPT) photoinitiator.

Further non-limiting examples of photoinitiators include, Acetophenone; Anisoin; Anthraquinone; Anthraquinone-2-sulfonic acid, sodium salt monohydrate; (Benzene) tricarbonylchromium; Benzil; Benzoin, sublimed; Benzoin ethyl ether; Benzoin isobutyl ether, tech.; Benzoin methyl ether; Benzophenone; Benzophenone/1-Hydroxycyclohexyl phenyl ketone, 50/50 blend; 3,3',4,4'-Benzophenonetetracarboxylic dianhydride, sublimed; 4-Benzoylbiphenyl; 2-Benzyl-2-(dimethylamino)-4'-morpholinobutyrophenone; 4,4'-Bis(diethylamino)benzophenone; 4,4'-Bis(dimethylamino) benzophenone; Camphorquinone; 2-Chlorothioxanthen-9-one; Dibenzosuberenone; 2,2-Diethoxyacetophenone; 4,4'-Dihydroxybenzophenone; 2,2-Dimethoxy-2-phenylacetophenone; 4-(Dimethylamino)benzophenone; 4,4'-Dimethylbenzil; 2,5-Dimethylbenzophenone, tech.; 3,4-Dimethylbenzophenone; Diphenyl(2,4,6-trimethylbenzoyl)phosphine oxide/2-Hydroxy-2-methylpropiophenone, 50/50 blend; 4'-Ethoxyacetophenone; 2-Ethylanthraquinone; 3'-Hydroxyacetophenone; 4'-Hydroxyacetophenone; 3-Hydroxybenzophenone; 4-Hydroxybenzophenone; 1-Hydroxycyclohexyl phenyl ketone; 2-Hydroxy-2-methylpropiophenone; 2-Methylbenzophenone; 3-Methylbenzophenone; Methylbenzoylformate; 2-Methyl-4'-(methylthio)-2-morpholinopropiophenone; Phenanthrenequinone; 4'-Phenoxyacetophenone; Thioxanthen-9-one; Triarylsulfonium hexafluoroantimonate salts, mixed, 50% in propylene carbonate; and Triarylsulfonium hexafluorophosphate salts, mixed, 50% in propylene carbonate.

A.1.2 Redox Initiator System

A redox initiator system includes an oxidizing agent (or an oxidizing component such as a peroxide) and a reducing agent (or a reducing component such as an aromatic or aliphatic amine). Combining the redox couple results in the generation of an initiating species (such as free radicals or cations) capable of causing curing.

In an embodiment, the redox couples are activated at temperatures below about 40° C., for example, at room temperature or at the physiological temperature of about 37° C. Generally, the redox couple is partitioned into separate reactive compositions prior to use and then subsequently mixed at the time of use to generate the desired initiating species. A desirable oxidizing agent is one that is sufficiently oxidizing in nature to oxidize the reducing agent, but not excessively oxidizing that it may prematurely react with other components with which it may be combined during storage. Similarly, a desirable reducing agent is one that is sufficiently reducing in nature to readily react with the preferred oxidizing agent, but not excessively reducing in nature such that it may reduce other components with which it may be combined during storage.

Suitable oxidizing agents include peroxide compounds (i.e., peroxy compounds), including hydrogen peroxide as well as inorganic and organic peroxide compounds. Examples of suitable oxidizing agents include, but are not limited to, peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert-butyl peroxide, tetraline peroxide, urea peroxide, and cumene peroxide; hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1, ammonium persulfate, sodium perborate, sodium perchlorate, potassium persulfate, etc.; ozone, ozonides, etc. These oxidizing agents may be used alone or in combinations with one another. One or more oxidizing agents may be present in an amount sufficient to provide initiation of the curing process. In some embodiments, about 0.01 weight percent (wt-%) to about 4.0 wt-%, of the one or more oxidizing agents are used. In other embodiments about 0.05 wt-% to about 1.0 wt-%, based on the total weight of the polymerizable composition are used.

A reducing agent has one or more functional groups for activation of the oxidizing agent. Preferably, such functional group(s) is selected from amines, mercaptans, or mixtures thereof. If more than one functional group is present, they may be part of the same compound or provided by different compounds. Exemplary reducing agents include a tertiary aromatic amines (e.g., N,N-dimethyl-p-toluidine (DMPT) or N,N-bis(2-hydroxyethyl)-p-toluidine (DHEPT)). Tertiary amines are well known in the art and can be found, for example, in WO 1997/35916 and U.S. Pat. No. 6,624,211, both of which are incorporated herein in their entirety, are also suitable for use as reducing agents.

Other reducing agents include mercaptans, sulfinic acids, formic acid, ascorbic acid, and hydrazines and metal salts.

A.1.3 Thermal Initiator

Non-limiting examples of a thermal initiator include a peroxydicarbonate, persulfate (e.g., potassium persulfate or ammonium persulfate), an azo initiator such as azosisobutyronitrile (AIBN), and various peroxides (e.g., benzoyl peroxide). Thermally activated initiators, alone or in combination with other type of initiators, are most useful where light cannot reach (e.g., deep within the curable admixture).

A.2. Monomers

A.2.1. Vinyl Ester Monomers

Many of the vinyl ester monomers suitable for use in the present invention are commercially available and other suitable vinyl ester monomers that are not commercially available may be prepared in accordance with published literature procedures cited herein. The below Table 1A lists non-limiting examples of the chemical compounds that are suitable for use in the present invention and which are commercially available from the following chemical suppliers itemized as items a) through e). Table 1B lists reference chemical compounds also commercially available from the following chemical suppliers.

a): TCI Europe;
b): Ivoclar Vivadent;
c): Cognis (Photomer4006 F);
d): Sartomer (Sartomer 415); and
e): Sigma Aldrich.

TABLE 1A

| Vinyl Ester Monomers | |
|---|---|
| Name | Structure |
| AVE[a] (adipic acid divinyl ester) | |
| KVE (octanedioic acid divinyl ester) | |
| SEVE (sebacic acid divinyl ester) | |
| DVMPL (diethylene glycol bis[O-(O'-vinylmaleinoyl)-polyactate]) | |
| TFVE (trimeric fatty acid trivinyl ester) | |

TABLE 1A-continued

Vinyl Ester Monomers

| Name | Structure |
|---|---|
| TUVE (ω,ω'-3,6,9-trioxaundecanedioic acid divinyl ester) | 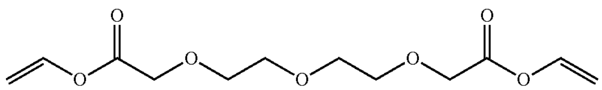 [SMILES: C=COC(=O)COCCOCCOCC(=O)OC=C] |

In another embodiment, the vinyl esters are selected from the group consisting of:

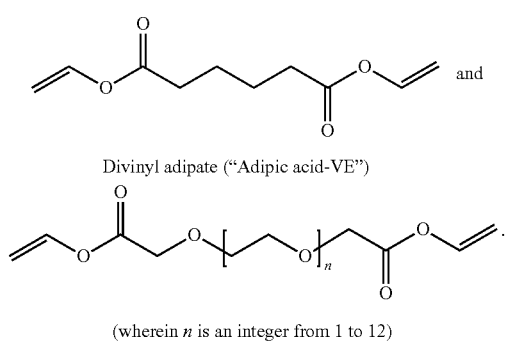

Divinyl adipate ("Adipic acid-VE")

(wherein n is an integer from 1 to 12)

In another embodiment, the vinyl esters are selected from the group consisting of:

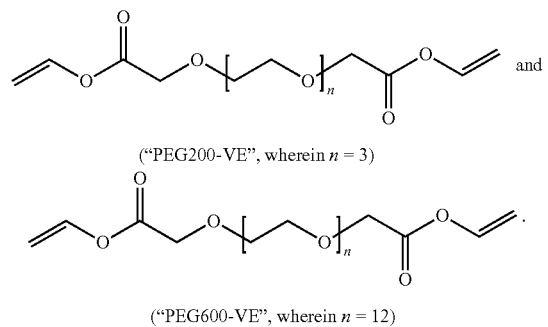

("PEG200-VE", wherein n = 3)

("PEG600-VE", wherein n = 12)

Reference acrylates and methacrylates that may be used as comparators in the present invention include acrylate and methacrylate monomers of the following general formulas.

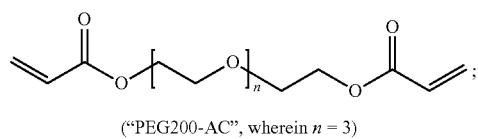

("PEG200-AC", wherein n = 3)

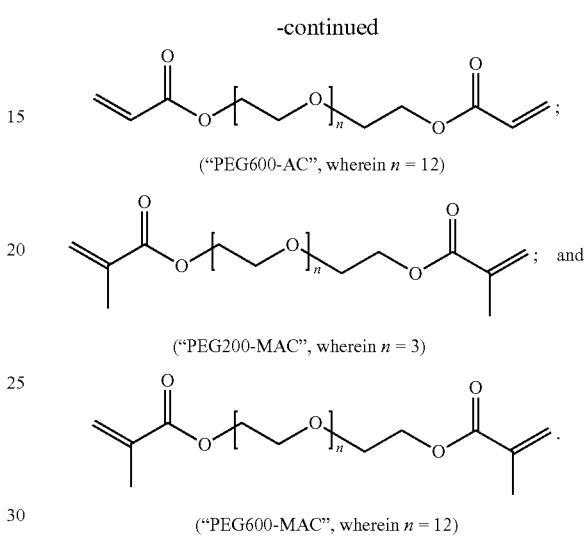

("PEG600-AC", wherein n = 12)

("PEG200-MAC", wherein n = 3)

("PEG600-MAC", wherein n = 12)

A.2.2. Vinyl Carbonate Monomers

Vinyl carbonates suitable for use in the present invention may be prepared in accordance with published literature procedures, including those detailed in the following literature references, all of which are incorporated herein in their entirety: R. A. Olofson and J. Cuomo, Tetrahedron Lett. 21(9), 819-22 (1980), describe the synthesis of isobutyl vinyl carbonate from trimethylsilyl vinyl ether and chlorofutnaric acid isobutylester using benzyltrimethylammonium fluoride as a catalyst; R. A. Olofson, Dang Vu Anh; D. S. Morrison, and P. F. De Cusati, J. Org. Chem. 55(1), 1-3 (1990), describe a one-step synthesis from chloro- or fluorofumaric acid esters and aldehyds using crown ether catalysis; and K. Rege, S. Hu, J. A. Moore, J. S. Dordick, and S. M. Cramer, J. Am. Chem. Soc. 126(39), 12306-12315 (2004), describe the chemoenzymatic and thus regioselective synthesis starting from methyleneoxime vinyl carbonate and alcohols.

In an embodiment, vinyl carbonate monomers suitable for use in the present invention include vinyl carbonates represented by the following structures.

| Name | Structure |
|---|---|
| EGDVC (ethylene glycol bis(vinyl carbonate)) | 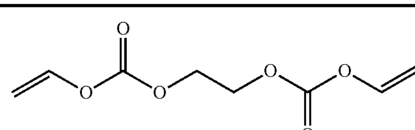 |

| Name | Structure |
|---|---|
| BDDVC (1,4-butanediol bis(vinyl carbonate)) | 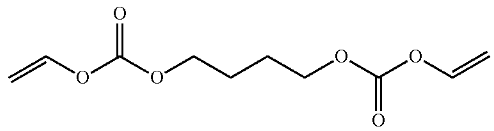 [SMILES: C=COC(=O)OCCCCOC(=O)OC=C] |
| HDDVC (1,6-hexanediol bis(vinyl carbonate)) | 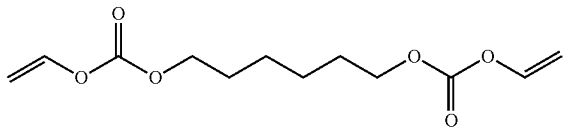 [SMILES: C=COC(=O)OCCCCCCOC(=O)OC=C] |
| GTVC (glycerine tris(vinyl carbonate)) | 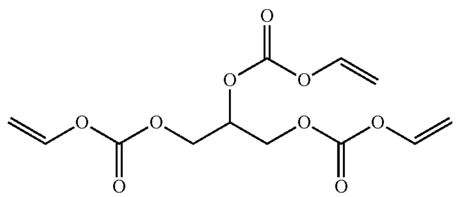 [SMILES: C=COC(=O)OCC(COC(=O)OC=C)OC(=O)OC=C] |
| DEGDVC (diethylene glycol bis(vinyl carbonate)) | 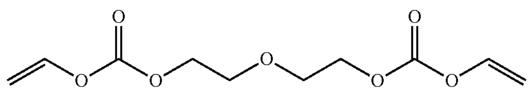 [SMILES: C=COC(=O)OCCOCCOC(=O)OC=C] |
| PEGDVC (polyethylene glycol(400) bis(vinyl carbonate)) | 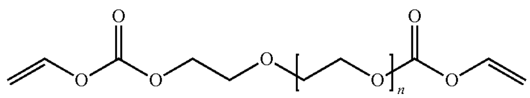 |
| RiTVC (ricinus oil tris(vinyl carbonate)) | 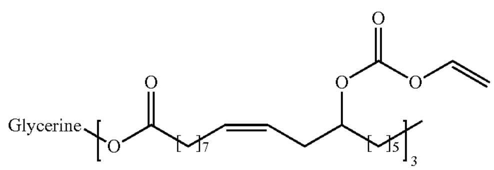 |
| HRiTVC (hydrated ricinus oil tris(vinylcarbonate)) | 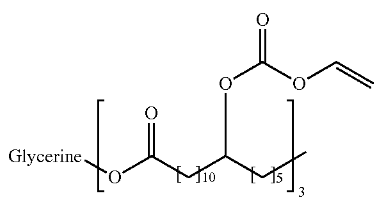 |
| DEG(PLAVC)$_2$ (diethylene glycol bis[O-(O'-vinyloxycarbonyl)-polylacetate]) | 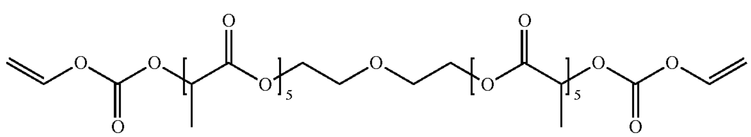 |

In another embodiment, vinyl carbonate monomers suitable for use in the present invention include vinyl carbonates represented by the following generic structures.

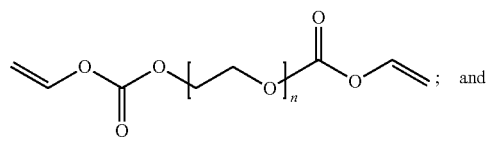
; and

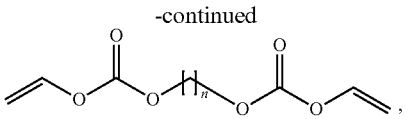

wherein n is an integer from 1 to 12

A.3. Multifunctional Thiols

Multifunctional thiols suitable for use in the present invention include multifunctional thiols represented by the following structures.

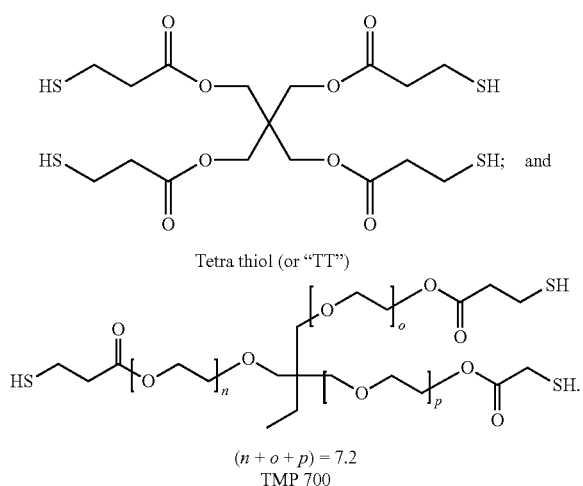

Tetra thiol (or "TT")

$(n + o + p) = 7.2$
TMP 700

Additional examples of suitable multifunctional thiols include THIOCURE® GDMA (Glycol Dimercaptoacetate); THIOCURE® TMPMA (Trimethylolpropane Trimercaptoacetate); THIOCURE® PETMA (Pentaerythritol Tetramercaptoacetate); THIOCURE® ETTMP 700 (Ethoxylated trimethylolpropane Tri-3-mercaptopropionate); THIOCURE® ETTMP 1300 (Ethoxylated trimethylolpropane Tri-3-mercaptopropionate); THIOCURE® PPGMP 800(polypropylene glycol (3-mercaptopropionate)); and THIOCURE® PPGMP 2200 (polypropylene glycol (3-mercaptopropionate)) all of which are readily available from BRUNO BOCK Chemische Fabrik GmbH & Co. KG, Eichholzer Str. 23, D-21463 Marschacht, Germany).

B. Other Considerations

The compositions of the present invention may optionally contain additives to provide certain desired properties. The amount of such additives is not specifically limited as long as the effects of the invention are not impaired. Preferably, the additives are selected from polymerization sensitisers and inhibitors, stabilizers, modifying agents, plasticizers, coloring agents, bioactive agents, cells such as osteoblasts and smooth muscle cells, thickeners, and filling agents. On the one hand, by means of these additives, plastic additives which are customary according to the state of the art may be introduced and, on the other hand, the behavior of the cured final product may be influenced. Thus, in especially preferred embodiments, the bioactive agents may be selected from drugs, proteins, and ligands of cell surface receptors. For example, thrombocyte aggregation inhibitors/blood-clotting inhibitors or immunosuppressants, but also peptides for influencing cell proliferation and cell differentiation may be introduced into the composition and/or may be attached to the surface of the cured polymer. Further, cell-selective proteins such as antibodies, e.g. anti-CD34 or anti-CD133, which may bind to stem or precursor cells via antigen/antibody-reactions, or complement inhibitors for preventing inflammations on the surface also belong to this group. Known agents for improving cell adherence such as carboxymethyl dextranes, proteoglycans, collagen, gelatine, glucosaminoglycans, fibronectin, lectins, polycations as well as natural and synthetic biological cell coupling agents such as RGD peptides may be introduced and/or attached to the surface. On the one hand, good cell adherence may be ensured this way and, on the other hand, the polymer obtained from the composition may function as drug carrier when used in combination with drugs in addition to or instead of its function as a substitute or supporting material for specific body tissues.

One or more substances that promote and/or induce bone formation may be incorporated into the compositions of the present invention. Non-limiting examples of such bone promoting materials include growth factors such as bone morphogenetic protein ("BMP") (Sulzer Orthopedics), BMP-2 (Genetics Institute/Sofamor Danek), basic fibroblast growth factor (bFGF) (Orquest/Anika Therapeutics), Epogen (Amgen), granulocyte colony-stimulating factor (G-CSF) (Amgen), Interleukin growth factor (IGF)-1 (Celtrix Pharmaceuticals), osteogenic protein (OP)-1 (Creative BioMolecules/Stryker Biotec), platelet-derived growth factor (PDGF) (Chiron), stem cell proliferation factor (SCPF) (University of Florida/Advanced Tissue Sciences), recombinant human interleukin (rhIL) (Genetics Institute), transforming growth factor beta (TGRβ) (Collagen Corporation/Zimmer Integra Life Sciences), and TGFβ-3 (OSI Pharmaceuticals). Bone formation may be reduced from several months to several weeks. In orthopedic and dental applications, bone regenerating molecules, seeding cells, and/or tissue can be incorporated into the compositions. For example bone morphogenic proteins such as those described in U.S. Pat. No. 5,011,691, the disclosure of which is incorporated herein by reference in its entirety, may be used in these applications.

Other filling materials for use in the present compositions include any forms of tricalcium phosphates, which, on the one hand, serve as a calcium source for the formation of bones and, on the other hand, improve the adherence of cells, as well as various organic fillers such as autologous serum or plasma of the transplant recipient.

Porosity forming agents may be used in the present compositions so long as they do not impair the properties of the resulting polymers. Non-limiting examples of substances that may be included in the compositions of the present invention include: particles of inorganic salts such as NaCl, $CaCl_2$, porous gelatin, carbohydrate (e.g., monosaccharide), oligosaccharide (e.g., lactose), polysaccharide (e.g., a polyglucoside such as dextrane), gelatin derivative containing polymerizable side groups, porous polymeric particles, waxes, such as paraffin, bees wax, and carnuba wax, and wax-like substances, such as low melting or high melting low density polyethylene (LDPE), and petroleum jelly. Other materials include hydrophilic materials such as PEG, alginate, bone wax (fatty acid dimers), fatty acid esters such as mono-, di-, and tri-glycerides, cholesterol and cholesterol esters, and naphthalene. In addition, synthetic or biological polymeric materials such as proteins can be used.

The size or size distribution of the porosity forming agent particles used in the invention can vary according to the specific need. Preferably the particle size is less than about 5000 μm, more preferably between about 500 and about 5000 μm, even more preferably between about 25 and about 500 μm, and most preferably between about 100 and 250 μm.

Non-limiting examples of prophylactic and/or therapeutic agents that may be incorporated into the composition of the present invention include antipyretic analgesic anti-inflammatory agents, including non-steroidal anti-inflammatory drugs (NSAIDs) such as indomethacin, aspirin, diclofenac sodium, ketoprofen, ibuprofen, mefenamic acid, azulene, phenacetin, isopropylantipyrin, acetaminophen, benzydamine hydrochloride, phenylbutazone, flufenamic acid, mefenamic acid, sodium salicylate, choline salicylate, sasapyrine, clofezone or etodolac; and steroidal drugs such as dexamethasone, dexamethasone sodium sulfate, hydrocortisone, prednisolone; antibacterial and antifungal agents such as penicillin, ampicillin, amoxicillin, cefalexin, erythromycin ethylsuccinate, bacampicillin hydrochloride, minocycline hydrochloride, chloramphenicol, tetracycline, erythromycin, fluconazole, itraconazole, ketoconazole, miconazole, terbinafine, piromidic acid, pipemidic acid trihydrate, enoxacin, cinoxacin, ofloxacin, norfloxacin, ciprofloxacin hydrochloride, or sulfamethoxazole trimethoprim; and anti-viral agents such as trisodium phosphonoformate, didanosine, dideoxycytidine, azido-deoxythymidine, didehydro-deoxythymidine, adefovir dipivoxil, abacavir, amprenavir, delavirdine, efavirenz, indinavir, lamivudine, nelfinavir, nevirapine, ritonavir, saquinavir or stavudine; high potency analgesics such as codeine, dihydrocodeine, hydrocodone, morphine, dilandid, demoral, fentanyl, pentazocine, oxycodone, pentazocine or propoxyphene; and salicylates which can be used to treat heart conditions or as an anti-inflammatory.

The agents can be incorporated in the composition directly, or can be incorporated in microparticles which are then incorporated in the composition. Incorporating the agents in microparticles can be advantageous for those agents which are reactive with one or more of the components of the composition.

One or more diagnostic agents may be incorporated into the compositions of the present invention. Diagnostic/imaging agents can be used which allow one to monitor bone repair following implantation of the compositions in a patient. Suitable agents include commercially available agents used in positron emission tomography (PET), computer assisted tomography (CAT), single photon emission computerized tomography, X-ray, fluoroscopy, and magnetic resonance imaging (MRI). Examples of suitable agents useful in MRI include the gadolinium chelates currently available, such as diethylene triamine pentaacetic acid (DTPA) and gadopentotate dimeglumine, as well as iron, magnesium, manganese, copper and chromium. Examples of suitable agents useful for CAT and X-rays include iodine based materials, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte. These agents can be detected using standard techniques available in the art and commercially available equipment.

"Electromagnetic radiation" as used herein refers to energy waves of the electromagnetic spectrum including, but not limited to, X-ray, ultraviolet, visible, infrared, far infrared, microwave, radio-frequency, sound and ultrasound waves.

"X-ray" as used herein refers to energy waves having a wavelength of $1 \times 10^{-9}$ to $1 \times 10^{-6}$ cm.

"Ultraviolet light" as used herein refers to energy waves having a wavelength of at least approximately $1.0 \times 10^{-6}$ cm but less than $4.0 \times 10^{-5}$ cm.

"Visible light" as used herein refers to energy waves having a wavelength of at least approximately $4.0 \times 10^{-5}$ cm to about $7.0 \times 10^{-5}$ cm.

"Blue light" as used herein refers to energy waves having a wavelength of at least approximately $4.2 \times 10^{\times 5}$ cm but less than $4.9 \times 10^{-5}$ cm.

"Red light" as used herein refers to energy waves having a wavelength of at least approximately $6.5 \times 10^{\times 5}$ cm but less than $7.0 \times 10^{-5}$ cm.

"Infrared" as used herein refers to energy waves having a wavelength of at least approximately $7.0 \times 10^{-5}$ cm.

Audible sound waves are in frequency ranges from 20 to 20,000 Hz.

Infrasonic waves are in frequency ranges below 20 Hz.

Ultrasonic waves are in frequency ranges above 20,000 Hz.

"Radiation source" as used herein refers to a source of electromagnetic radiation. Examples include, but are not limited to, lamps, the sun, blue lamps, and ultraviolet lamps.

The curable composition of the present invention is subjected to an electromagnetic radiation from a radiation source for a period sufficient to cure the curable composition to form a biodegradable, resorbable polymer. Preferably, the curable composition is applied in layer(s) of 1-10 mm, more preferably about 3-5 mm, and subjected to an electromagnetic radiation for about 30 to 300 seconds, preferably for about 50 to 100 seconds, and more preferably for about 60 seconds.

Typically, a minimum of 0.01 mW/cm$^2$ intensity is needed to induce polymerization. Maximum light intensity can range from 1 to 1000 mW/cm$^2$, depending upon the wavelength of radiation. Tissues can be exposed to higher light intensities, for example, longer wavelength visible light, which causes less tissue/cell damage than shortwave UV light. In dental applications, blue light (470-490 nm) is used at intensities of 100 to 400 mW/cm$^2$ clinically. When UV light is used in situ, it is preferred that the light intensity is kept below 20 mW/cm$^2$.

In another embodiment, when a thermally activated initiator is used (alone or in combination with other type(s) of initiator(s)), the curable composition is subjected to a temperature suitable for activating the thermally activated initiators, preferably the temperature from about 20 to 80° C., more preferably from about 30 to 60° C. Heat required to activate the thermal activator can be generated by various known means, and depending on whether the photopolymerization is carried out in situ or in vitro, the choice of heat source can include, but not limited to infrared, water bath, oil bath, microwave, ultrasound, or mechanical means, such as heating the curable composition in a crucible using a hot water bath.

In another embodiment, when a redox initiator system is used (alone or in combination with other type(s) of initiator(s)), the oxidizing agent of the redox initiator system is kept apart from the reducing agent of the redox initiator system until immediately before the curing process. For example, the oxidizing agent is mixed with some curable composition in one container and the reducing agent is mixed with some curable composition in another container. The contents of the two containers are then mixed with each other to cause curing of the curable composition.

The curing can take place in situ, ex vivo or in vivo. In an embodiment, in order to shorten the duration of the radiation exposure and/or increase the thickness of each radiation curable layer, a redox initiator system is used in combination with a photoinitiator and/or thermal initiator. For example, the redox initiator system is activated first to partially cure the curable composition. Such partially cured composition is then subjected to radiation and the photoinitiator and/or thermal initiator is activated to further cure the partially cured composition.

C. Properties of the Curable Composition and the Cured Polymer

Generally the vinyl ester and vinyl carbonate compositions and cured polymer composites described herein are much less toxic than (meth)acrylates; have photoreactivity dramatically increased by thiols; have enhanced impact resistance; and exhibit non-toxic degradation products of polymer [poly(vinyl alcohol)] and non-reactive groups (acetaldehyde vs. acrylic acid). Furthermore, the compositions of the present invention have mechanical properties that are tunable. Among the several properties of the curable compositions and the cured polymer composites disclosed herein that can be tuned are the following.

C.1 Viscosity

The viscosity of the curable composition can be varied by modulating a number of factors, including the molecular weight of the ingredients in the curable composition, and the temperature of the curable composition. Typically, when the temperature is low, the curable composition is more viscous; and, when the average molecular weight of the ingredients is high, it becomes more viscous. Different applications of the curable composition also may require different viscosities. For example, to be injectable, the curable composition must be a free flowing liquid and, in other applications, a moldable paste-like putty may be more suitable.

C.2. Strength

It is preferred that the strength of the cured polymer be from about 5 to 300 N/m$^2$; more preferably from about 20 to 200 N/m$^2$; and most desirably from about 50 to 200 N/m$^2$. The strength of the cured polymer may be modulated by adjustment of a number of factors, including the ratio the excipients and/or the monomers, and the density of the cured polymer.

C.3. Hydrophobicity/Hydrophilicity

The hydrophobicity/hydrophilicity of the photoplymerizable composition and/or the cured polymer must be carefully controlled. Preferably, the curable composition and cured polymer are sufficiently hydrophilic that cells adhere well to them. The hydrophobicity/hydrophilicity depends on a number of factors, including the hydrophobicity/hydrophilicity of the excipients and/or monomers. For example, the ratio less hydrophilic components to the more hydrophilic may be adjusted to modulate the hydrophobicity/hydrophilicity of the cured polymer D. Applications of the Curable Composition and the Cured Polymer Compositions of the present invention result polymers that are suitable for use in various biomedical applications. In particular, the present compositions are suitable for use in any site in the body where heavy load is not experienced, including CNS area, the mandible, the skull, and the spine.

D.1. Vertebroplasty and Kyphoplasty

Vertebroplasty and kyphoplasty are minimally invasive procedures for the treatment of vertebral compression fractures ("VCF"), or fractures involving the vertebral bodies that make up the spinal column. When a vertebral body fractures, the usual rectangular shape of the bone becomes compressed, causing pain. In some instances, these compression fractures may involve collapse of one or more vertebrae in the spine, commonly caused by osteoporosis. Osteoporosis results in a loss of normal bone density, mass and strength, leading to a condition in which bones are increasingly porous, and vulnerable to breaking. Vertebrae may also become weakened by cancer. Regardless of the cause of vertebrae weakening, the compositions and methods of the present invention may be used to effect in situ augmentation of the vertebral structure in a patient's vertebrae that weakened by disease or bone fracture due, for example, to physical trauma. In vertebroplasty, health professionals may use image guidance to inject the composition of the present invention into a fractured or weakened vertebra/bone through a hollow needle; and thereafter direct radiation (e.g. light) to cause radical polymerization of the injected composition to thereby augment the fracture vertebra/bone. In kyphoplasty, a balloon is first inserted into the fractured (or weakened) vertebra/bone through a hollow needle to create a cavity or space in the fractured (or weakened) vertebra/bone. The composition of the present invention is then injected into the cavity/space following the removal of the balloon.

D.2. Dental Applications

The curable composition and cured polymer of the present invention can be used to fill extraction sockets; prevent or repair bone loss due to tooth extraction; repair jaw bone fractures; fill bone voids due to disease and trauma; stabilize an implant placed into an extraction socket and/or one placed into an edentulous jawbone to provide immediate function (e.g., chewing); provide ridge (of bone) augmentation; repair periodontal bone lesions; and provide esthetic gingiva reshaping and plumping. When the curable composition and/or the cured polymer are used for dental implant applications, preferably, the dental implant is partially or fully embedded into the cured polymer.

D.3. Orthopedic Applications

The curable composition and cured polymer of the present invention can be used to repair bone fractures, repair large bone loss (e.g., due to disease) and provide immediate function and support for non-load-bearing bones; as well as to cosmetically enhance profile of body parts such as chin, cheek, and the like. The curable composition can be applied using standard orthopedic or surgical techniques; e.g., it can be applied to a site where bone generation is desired and cured to form the cured polymer. The curable composition may also be pre-cast into a desired shape and size (e.g., rods, pins, screws, plates, and prosthetic devices such as for the skull, chin and cheek) and cured to form the cured polymeric structure ex vivo.

D.4. Contact Lenses

The curable composition and cured polymer of the present invention can be used to make contact lenses. In some embodiments, the contact lenses made using curable composition and cured polymer of the present invention may be configured as an ocular drug delivery system, for example, as drug-eluting contact lenses for the for the treatment of periocular and intraocular diseases. Examplary ocular diseases include, but are not limited to, cataract, age-related macular degeneration, diabetic retinopathy, and glaucoma. Advantages of ocular drug delivery system include increased ocular bioavailability, prolonged residence time, improved patient compliance, higher efficiency and low side effects compared to conventional dosage forms.

D.5. Rapid Prototyping and Three-Dimensional Printing (3DP)

The curable compositions of the present invention may be adapted for rapid prototyping (RP) as well as three-dimensional printing (3DP) of implants. Using digital light processing, for example, the curable compositions of the present invention may be fabricated into implants, including dental implants.

These and other aspects of the present invention will be further appreciated upon consideration of the following Examples, which are intended to illustrate certain particular embodiments of the invention but are not intended to limit its scope, as defined by the claims.

Chemicals Used

| chemical | structure | CAS-No. | producer |
|---|---|---|---|
| Adipic acid-VE (Hexanedioic acid divinyl ester) | 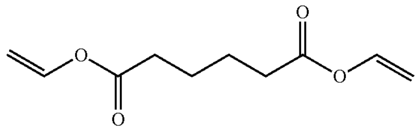 | 4074-90-2 | TCI Europe |
| Butanediol-AC (1,4-Butanediol-diacrylate) | 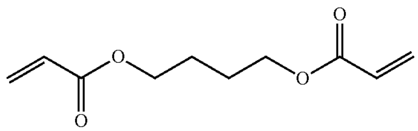 | 19485-03-1 | Sigma Aldrich |
| PEG200-AC (Tetra(ethylene glycol) diacrylate) | 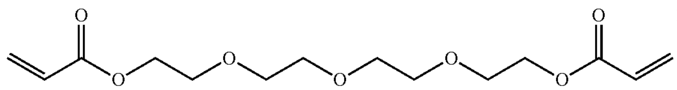 [SMILES: C=CC(=O)OCCOCCOCCOCCOC(=O)C=C] | 17831-71-9 | Sigma Aldrich |
| PEG600-AC (Poly(ethylene glycol) diacrylate, MG 600) | 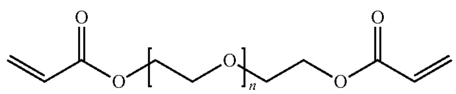 | 26570-48-9 | Sigma Aldrich |
| Butanediol-MAC (1,4-Butanediol dimethacrylat) | 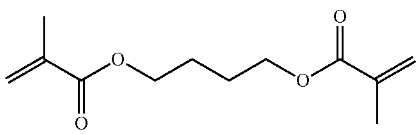 [SMILES: C=C(C)C(=O)OCCCCOC(=O)C(=C)C] | 1189-08-8 | Sigma Aldrich |
| PEG200-MAC (Tetra(ethylene glycol) dimethacrylate) | 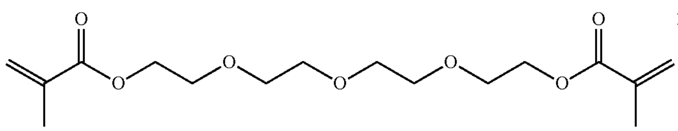 [SMILES: C=C(C)C(=O)OCCOCCOCCOCCOC(=O)C(=C)C] | 109-17-1 | UCB Chemicals |
| PEG600-MAC (Poly(ethylene glycol) dimethacrylate, MG 600) | 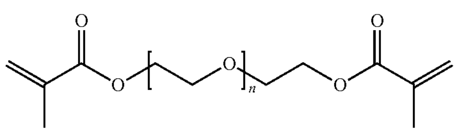 | 25852-47-5 | Sigma Aldrich |

EXAMPLES

Example 1A

Synthesis of Vinyl Esters

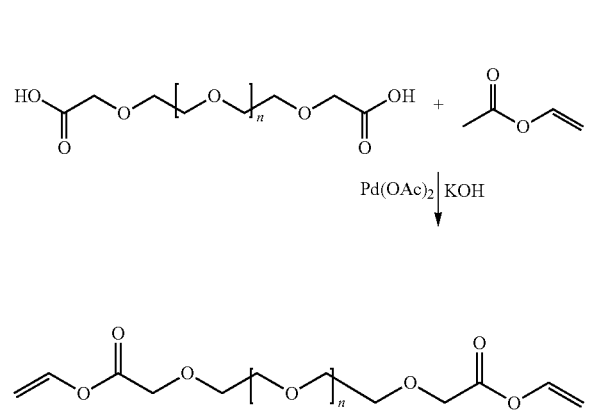

n = 1 TUVE
n = 2.1 PEG250DVE
n = 9.2 PEG600DVE

Synthesis of 3,6,9-trioxaundecanedioic acid divinyl ester (TUVE)

Reactants:

| | | |
|---|---|---|
| 3,6,9-trioxaundecanedioic acid | 15.1 g | (68.7 mmol) |
| vinyl acetate | 175 g | |
| Pd(OAc)$_2$ | 0.75 g | (3.34 mmol) |
| KOH | 0.38 g | (6.79 mmol). |

Procedure:

15.1 g (68.7 mmol) 3,6,9-trioxaundecanedioic were dissolved in 175 g vinyl acetate and 0.75 g (3.34 mmol) of the Pd-catalyst and 0.38 g (6.79 mmol) powdered potassium hydroxide were added to the solution. The mixture was heated to 60° C. for 48 h under argon atmosphere. The reaction mixture was allowed to cool down to room temperature, filtrated and washed with ethyl acetate (50 mL). The filtrate was extracted with water (2×50 mL), dried over Na$_2$SO$_4$, filtered and concentrated. The orange colored residue was purified by kugelrohr distillation (140° C./0.3 mbar).

Yield: 6.2 g (33% of th.) of a colorless liquid
TLC (PE:EE=1:1) R$_f$=0.65
1H-NMR (CDCl$_3$): δ (ppm) 7.27 (2H, dd, J=13.9 Hz, J=6.3 Hz —O(C$\underline{H}$)=CH$_2$); 4.90 (2H, dd, J=13.9 Hz, J=1.7

Hz, $\underline{H}_2C{=}C$ trans); 4.61 (2H, dd, J=6.3 Hz, J=1.8 Hz, $\underline{H}_2C{=}C$ cis); 4.22 (4H, s, —$CH_2$—); 3.79-3.62 (8H, m, —O—$CH_2$—)

$^{13}C$-NMR (CDCl$_3$): δ (ppm): 167.7, 140.5, 98.5, 71.0, 70.7, 68.2.

IR (ATR, cm$^{-1}$): 2932, 2882, 1768, 1649, 1240, 1181, 1112, 949, 875.

GC-MS (m/z): 252.90, 207.04, 190.98, 129.07, 87.08.

Example 2

Synthesis of Poly(ethylene glycol-250)Diacetic Acid Divinyl Ester (PEG200-VE)

Reactants:

| | | |
|---|---|---|
| PEG250 diacetic acid | 50 g | (200 mmol) |
| vinyl acetate | 470 g | |
| Pd(OAc)$_2$ | 2.16 g | (9.62 mmol) |
| KOH | 1.08 g | (19.25 mmol) |

Procedure:

The synthesis was carried out analogously to synthesis example [TUVE] using poly(ethylene glycol)-250 diacetic acid. The orange colored residue was purified by column chromatography (PE:EE=5:1).

Yield: 21.62 g (36% of th.) of a colorless liquid

TLC (PE:EE=5:1) $R_f$=0.51

$^1$H-NMR (CDCl$_3$): δ (ppm) 7.32 (2H, dd, J=13.9 Hz, J=6.2 Hz —O(C$\underline{H}$)=$CH_2$); 4.94 (2H, dd, J=14.1 Hz, J=1.9 Hz, $\underline{H}_2C{=}C$ trans); 4.64 (2H, dd, J=6.2 Hz, J=1.7 Hz, $\underline{H}_2C{=}C$ cis); 4.26 (4H, s, —$CH_2$—); 3.83-3.69 (12H, m, —O—$CH_2$—).

Example 3

Synthesis of Poly(ethylene glycol-600) Diacetic Acid Divinyl Ester (PEG600-VE)

Reactants:

| | | |
|---|---|---|
| PEG600 diacetic acid | 27 g | (45 mmol) |
| vinyl acetate | 117.5 g | |
| Pd(OAc)$_2$ | 0.48 g | (2.14 mmol) |
| KOH | 0.24 g | (4.28 mmol) |

Procedure:

The synthesis was carried out analogously to synthesis Example 1 using poly(ethylene glycol)-600 diacetic acid. The crude product was extracted with saturated NaCl-solution (2×50 mL), dried over Na$_2$SO$_4$, filtered, and concentrated.

Yield: 23 g (78% of th.) of a colorless liquid $^1$H-NMR (CDCl$_3$): δ (ppm) 7.23 (2H, dd, J=13.9 Hz, J=6.3 Hz —O(C$\underline{H}$)=$CH_2$); 4.87 (2H, dd, J=13.9 Hz, J=1.8 Hz, $\underline{H}_2C{=}C$ trans); 4.59 (2H, dd, J=6.3 Hz, J=1.8, $\underline{H}_2C{=}C$ cis); 4.20 (4H, s, —$CH_2$—); 3.75-3.49 (54H, m, —O—$CH_2$—)

Example 4

Synthesis of Vinyl Carbonates

Synthesis of 1,4-butanediol divinyl carbonate (Butanediol-VC)

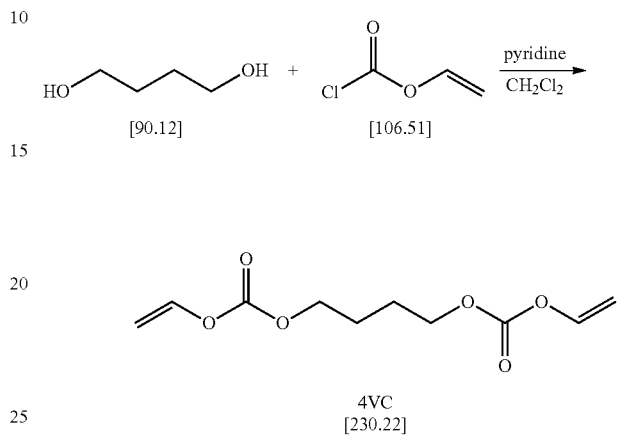

Reactants:

| | | |
|---|---|---|
| 1,4-butanediol | 1.50 g | (16.6 mmol) |
| chloroformic acid vinyl ester | 3.60 g | (33.8 mmol) |
| pyridine | 2.70 g | (34.3 mmol) |
| CH$_2$Cl$_2$ | 50 mL | |

Procedure:

A solution of 1.50 g (16.6 mmol) 1,4-butanediol and 2.70 g (34.3 mmol) pyridine in 50 ml CH$_2$Cl$_2$ was cooled to 0° C. and purged with argon. 3.60 g (33.8 mmol) chloroformic acid vinyl ester were added dropwise to the stirred solution over a period of 10 min using a syringe. After complete addition, the reaction mixture was allowed to warm up to room temperature and stirred for another 4 h. The reaction was hydrolyzed with 1 N HCl solution (15 mL), the organic layer was dried over Na$_2$SO$_4$, and filtered. After evaporation of the volatile compounds the crude product was purified by column chromatography (PE:EE=3:1). Alternatively, this compound could be purified by kugelrohr distillation (130° C./5 mbar).

Yield: 3.6 g (94% of th.) of a colorless liquid

TLC (PE:EE=3:1) Rf=0.77

$^1$H-NMR (CDCl$_3$): δ (ppm): 7.07 (2H, dd, J=13.8 Hz, J=6.2 Hz, $H_2C{=}C\underline{H}$—O); 4.91 (2H, dd, J=13.8 Hz; J=2.1 Hz, $\underline{H}_2C{=}CH$—O trans); 4.57 (2H, dd, J=6.2 Hz, J=2.1 Hz, $\underline{H}_2C{=}CH$—O, cis); 4.23 (4H, t, O—C$\underline{H}_2$), 1.81 (4H, q$_5$, $CH_2$)

$^{13}C$-NMR (CDCl$_3$): δ (ppm): 152.6, 142.5, 97.7, 67.8, 24.9

IR (ATR, cm$^{-1}$): 2968, 1756, 1651, 1234, 1156, 952, 875, 783

GC-MS (m/z): 231.03, 143.04, 117.08, 89.03, 81.08, 55.10

Example 5

Synthesis of Poly(ethylene glycol-200)Divinyl Carbonate (PEG200-VC)

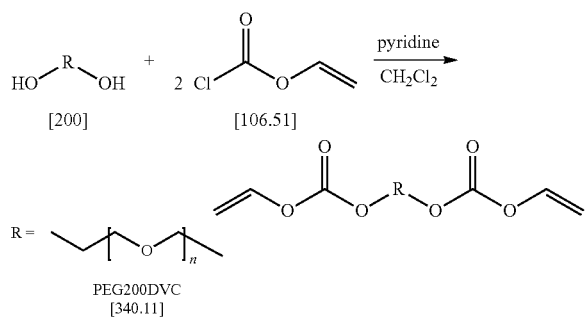

PEG200DVC
[340.11]

Reactants:

| | | |
|---|---|---|
| PEG200 | 5.0 g | (25 mmol) |
| chloroformic acid vinyl ester | 5.3 g | (50 mmol) |
| pyridine | 4.0 g | (50 mmol) |
| CH$_2$Cl$_2$ | 60 mL | |

Procedure:

The synthesis was carried out analogously to synthesis example 4 using poly(ethylene glycol)-200 and chloroformic acid vinyl ester. The orange colored residue was purified by column chromatography (PE:EE=1:2).

Yield: 8.0 g (94% of th.) of a colorless liquid

TLC (PE:EE=1:2) Rf=0.5

$^1$H-NMR (CDCl$_3$): δ (ppm): 7.05 (2H, dd, J=13.8 Hz, J=6.2 Hz, H$_2$C=CH—O); 4.88 (2H, dd, J=13.8 Hz; J=2.0 Hz, H$_2$C=CH—O trans); 4.54 (2H, dd, J=6.2 Hz, J=2.0 Hz, H$_2$C=CH—O, cis); 4.31 (4H, t, OCO—CH$_2$), 3.71 (4H, t, OC—O—CH$_2$—CH$_2$), 3.61 (8H, bs, O—CH$_2$)

$^{13}$C-NMR (CDCl$_3$): δ (ppm): 152.7, 142.6, 97.8, 70.6, 68.7, 67.5

IR (ATR, cm$^{-1}$): 2876, 1759, 1651, 1243, 1081, 946, 875, 813, 783

Example 6

Enhanced Reaction Velocity of Various Esters and Vinyl Carbonates at a Range of Thiol Concentration Enhanced reaction velocity of various esters and vinyl carbonates at a range of thiol concentration were measured in terms of time to reach the maximum of the polymerization heat [s] as is illustrated in Tables 2-7. The compositions which are embodiments of the present invention were compared to acrylate and methacrylate based polymer systems as comparative examples. In each instance illustrated in Tables 2-6, the vinyl ester and/or vinyl carbonate based compositions showed unexpected increase in reaction rate whereas the comparative examples showed either not change or a decrease in reaction rate.

TABLE 2

PEG600 Monomer Series with the Tetrathiol TT

| PEG600 | 0% TT | 10% TT | 20% TT | 40% TT |
|---|---|---|---|---|
| Acrylate | 3.2 | 3.2 | 3.0 | 3.0 |
| Methacrylate | 10.5 | 26.3 | 31.2 | 24.9 |
| Vinyl ester | 44.4 | 35.0 | 22.9 | 19.9 |

TABLE 3

PEG600 Monomer Series with the Trithiol TMP 700

| PEG600 | 0% TMP700 | 10% TMP700 | 20% TMP700 | 40% TMP700 |
|---|---|---|---|---|
| Acrylate | 3.2 | 3.8 | 3.7 | 3.2 |
| Methacrylate | 10.5 | 27.0 | 31.2 | 30.6 |
| Vinyl ester | 44.4 | 30.5 | 25.0 | 21.0 |

TABLE 4

PEG200 Monomer Series with the Tetrathiol TT

| PEG200 | 0% TT | 10% TT | 20% TT | 40% TT |
|---|---|---|---|---|
| Acrylate | 2.6 | 3.5 | 3.3 | 3.3 |
| Methacrylate | 12.6 | 51.5 | 58.3 | 54.0 |
| Vinyl ester | 36.7 | 17.2 | 14.4 | 11.9 |
| Vinyl carbonate | 13.6 | 14.3 | 14.1 | 9.9 |

TABLE 5

PEG200 Monomer Series with the Trithiol TMP 700

| PEG200 | 0% TMP700 | 10% TMP700 | 20% TMP700 | 40% TMP700 |
|---|---|---|---|---|
| Acrylate | 2.6 | 3.6 | 3.6 | 3.4 |
| Methacrylate | 12.6 | 56.0 | 55.1 | 46.9 |
| Vinyl ester | 36.7 | 23.6 | 16.0 | 13.0 |
| Vinyl carbonate | 13.6 | 12.1 | 5.1 | 2.5 |

TABLE 6

Butanediol Monomer Series with the Tetrathiol TT

| Butanediol | 0% TT | 10% TT | 20% TT | 40% TT |
|---|---|---|---|---|
| Acrylate | 2.7 | 2.5 | 2.8 | 2.7 |
| Methacrylate | 28.6 | 87.6 | 83.8 | 55.0 |
| Vinyl ester | 4.9 | 7.7 | 5.8 | 2.1 |
| Vinyl carbonate | 3.3 | 7.1 | 3.0 | 2.4 |

TABLE 7

Butanediol Monomer Series with the Trithiol TMP 700

| Butanediol | 0% TMP700 | 10% TMP700 | 20% TMP700 | 40% TMP700 |
|---|---|---|---|---|
| Acrylate | 2.7 | 2.9 | 3.5 | 3.5 |
| Methacrylate | 28.6 | 90.2 | 85.4 | 75.0 |
| Vinyl ester | 4.9 | 8.4 | 2.9 | 2.1 |
| Vinyl carbonate | 3.3 | 6.1 | 4.4 | 2.1 |

Example 7

Monomer Toxicity Tests

The cytotoxicity of the monomers: AVE, TUVE, PEG250DVE, PEG600DVE, TTEGDAc, and TTEGDMA, and pentaerythritol tetra(3-mercaptopropionate) (PTM), was examined in fibroblast cell culture by using an Alamar Blue Assay. This assay incorporated a fluorometric/colormetric growth indicator based on detection of metabolic activity. The results represent the mean with standard deviations of triplicate assays (n=3). The comparison of the estimated TC50-values, the concentration of monomer at which the activity of resorufin production was reduced to 50% of the control, are shown in table 8.

TABLE 8

TC50 values of various monomers

| Monomer | $TC_{50}$ [mM] |
|---|---|
| AVE | 10 |
| TUVE | 2.5 |
| PEG250DVE | 0.63 |
| PEG600DVE | 0.63 |
| TTEGDMA | <0.16 |
| TTEGDAc | <0.16 |
| PTM | 10 |

As shown in table 8, all synthesized monomers and the thiol PTM exhibited lower cytotoxicity compared to the (meth)acrylate-based compounds (TTEGDMA and TTEGDAc), by at least a factor of 4.

Example 8

Photoreactivity

Figure 2:
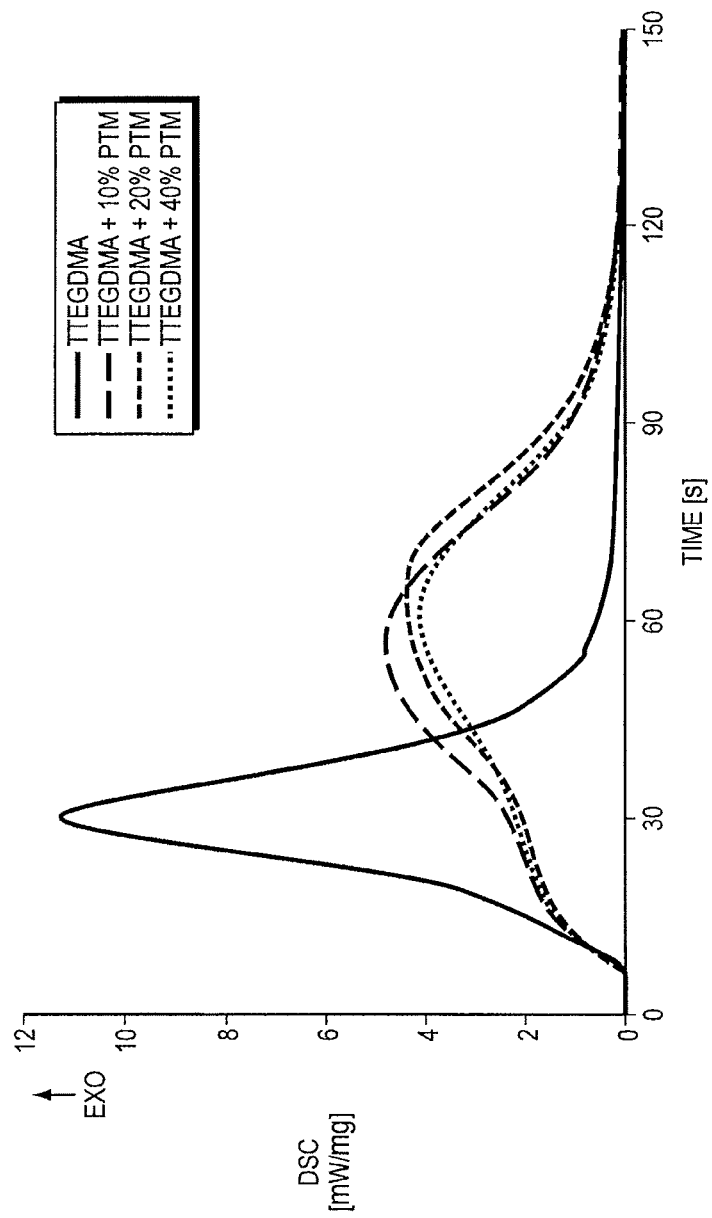
FIG. 2 illustrates photo-DSC measurements of TTEGDMA containing different amounts of the thiol PTM.
Figure 3:
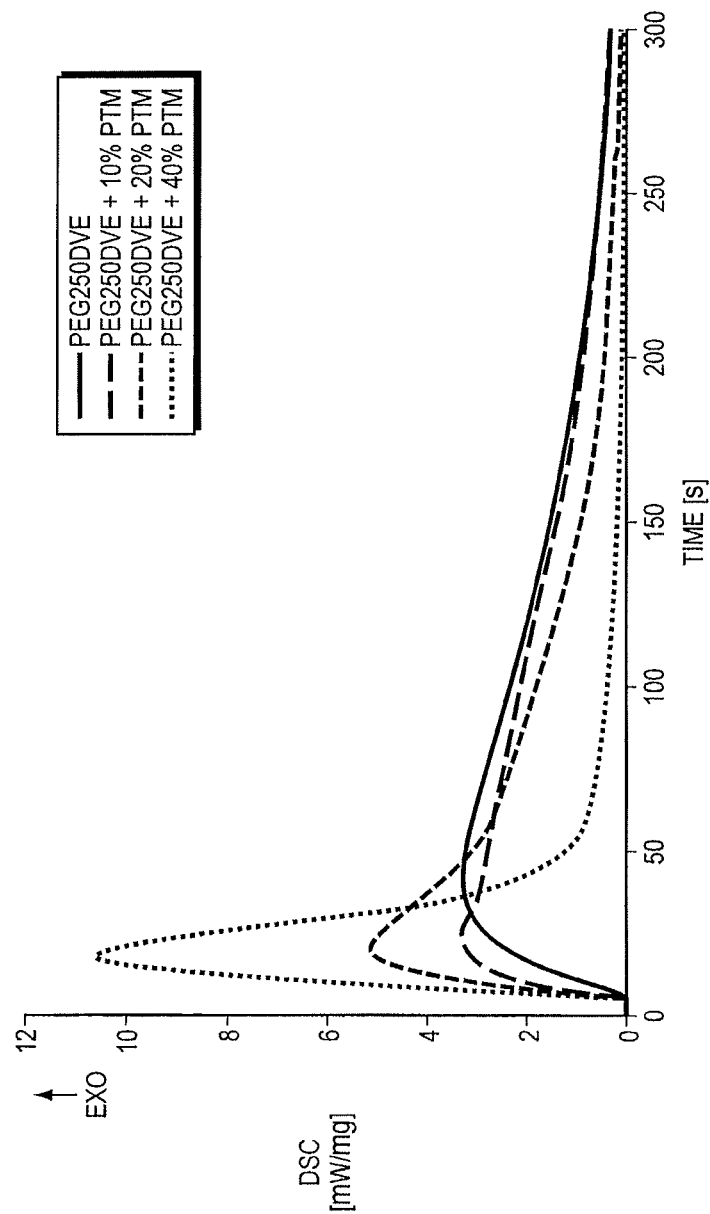
FIG. 3 illustrates photo-DSC measurements of PEG250DVE containing different amounts of the thiol PTM.
Figure 4:
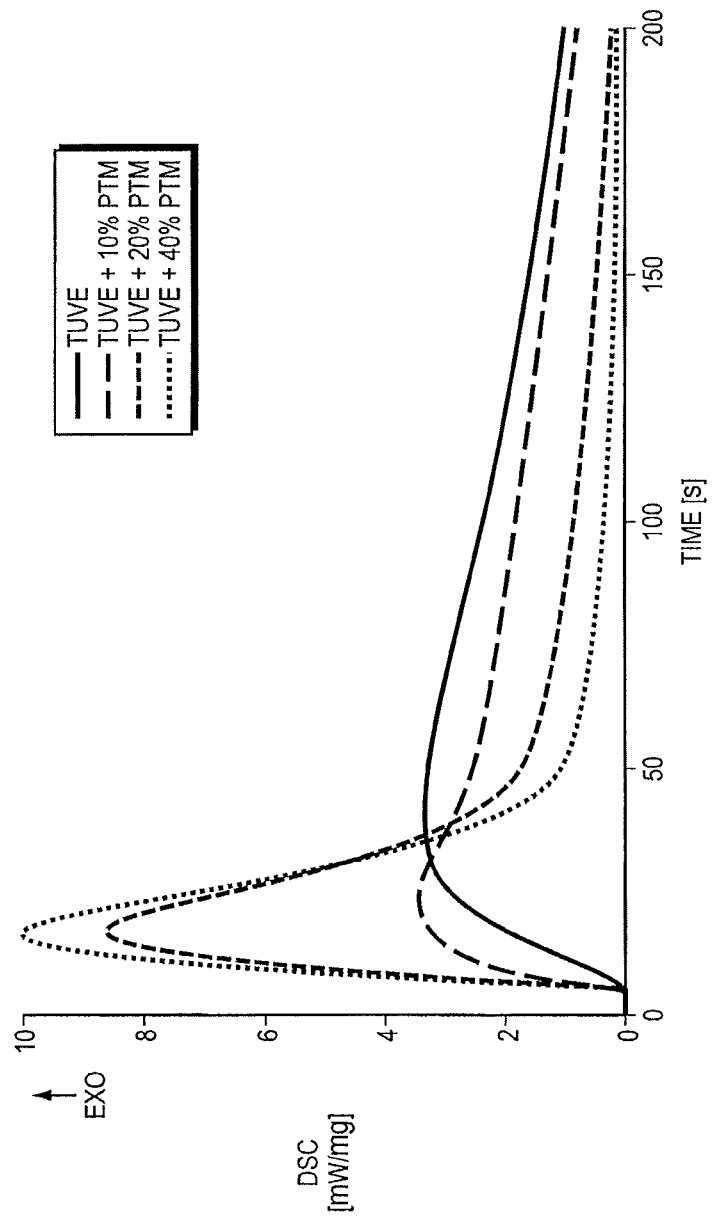
FIG. 4 illustrates photo-DSC measurements of TUVE containing different amounts of the thiol PTM.
Figure 5:
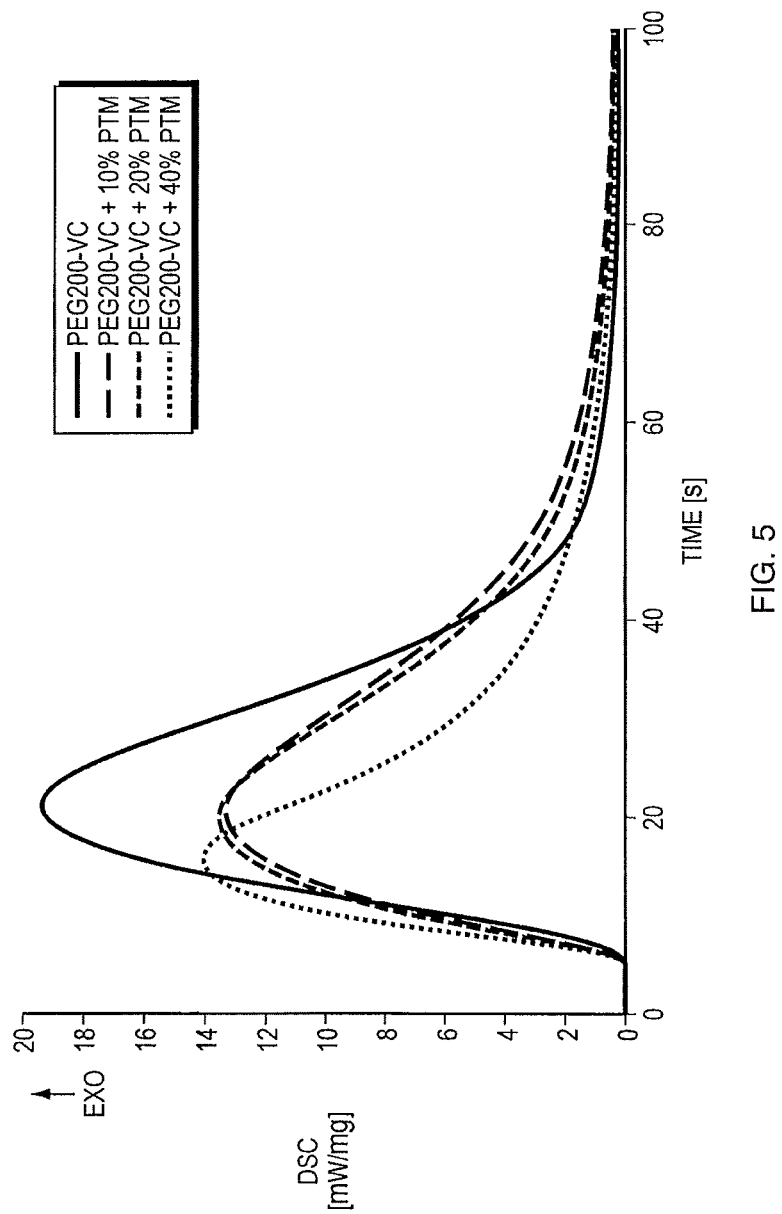
FIG. 5 illustrates photo-DSC measurements of PEG200-VC containing different amounts of the thiol PTM.
Figure 6:
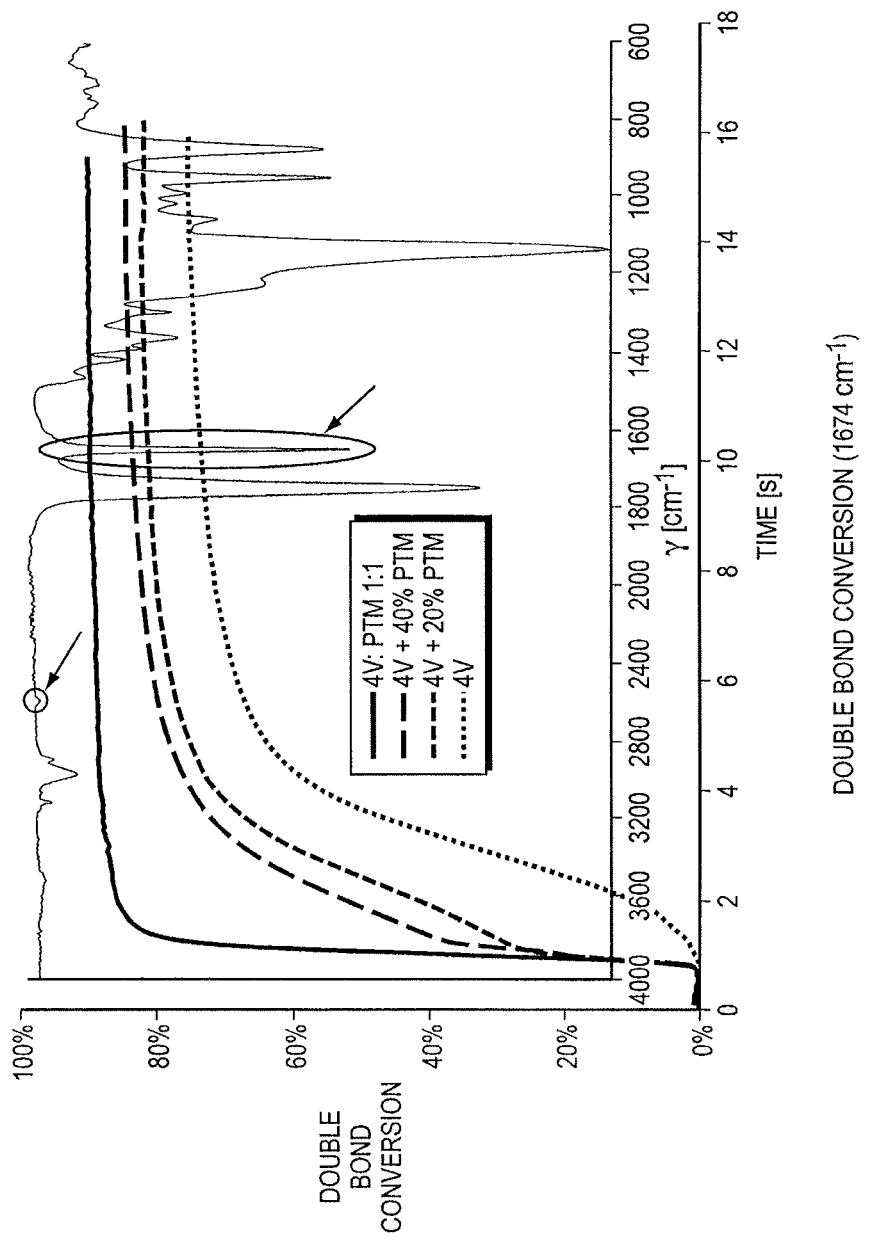
FIG. 6 illustrates Infra Red Spectroscopic monitoring of photoreactivity of the vinyl ester 4V in presence of various amounts of PTM.
Figure 7:
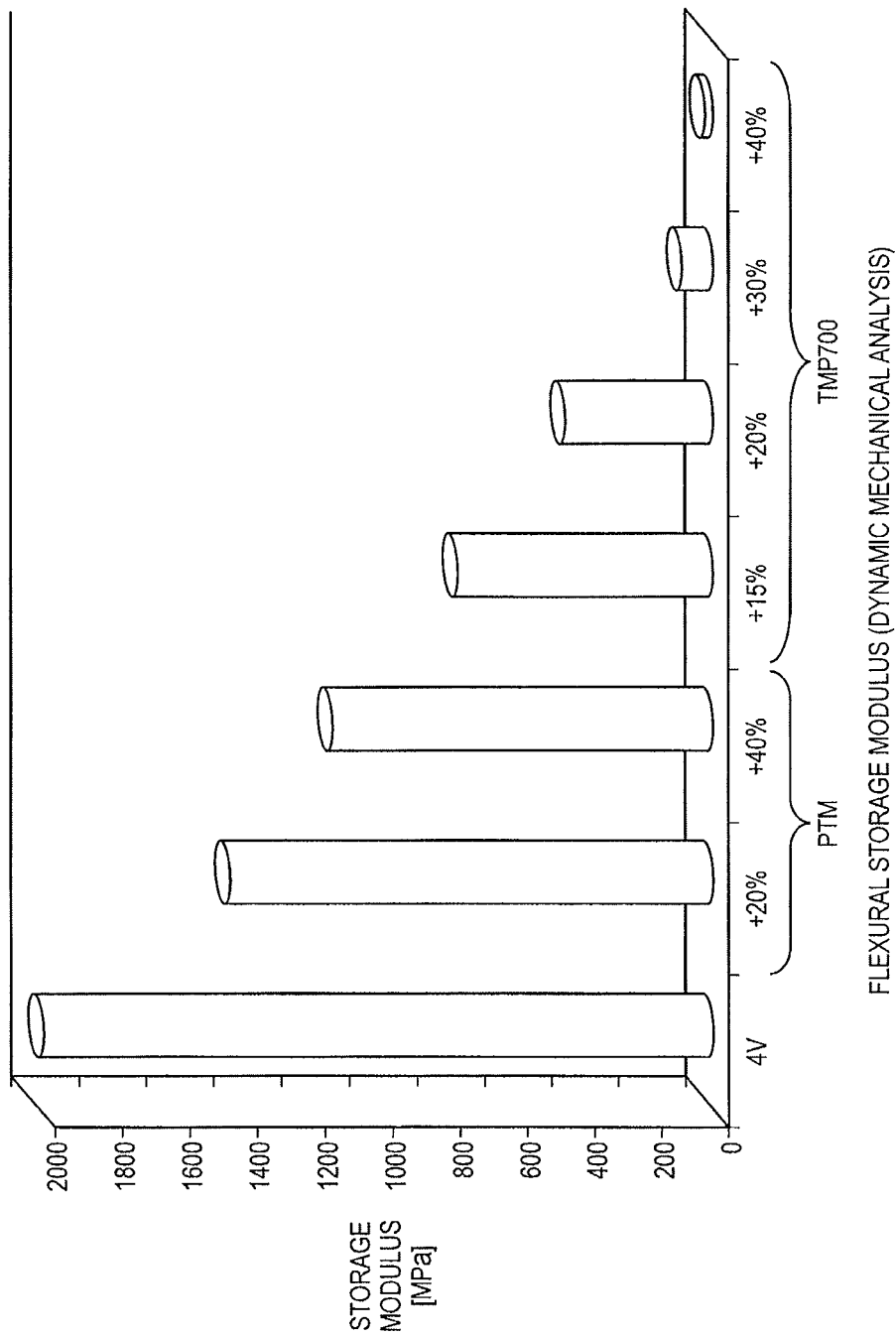
FIG. 7 illustrates Flexural storage modulus of the vinyl ester 4V in presence of various amounts of PTM and TMP700.
Figure 8:
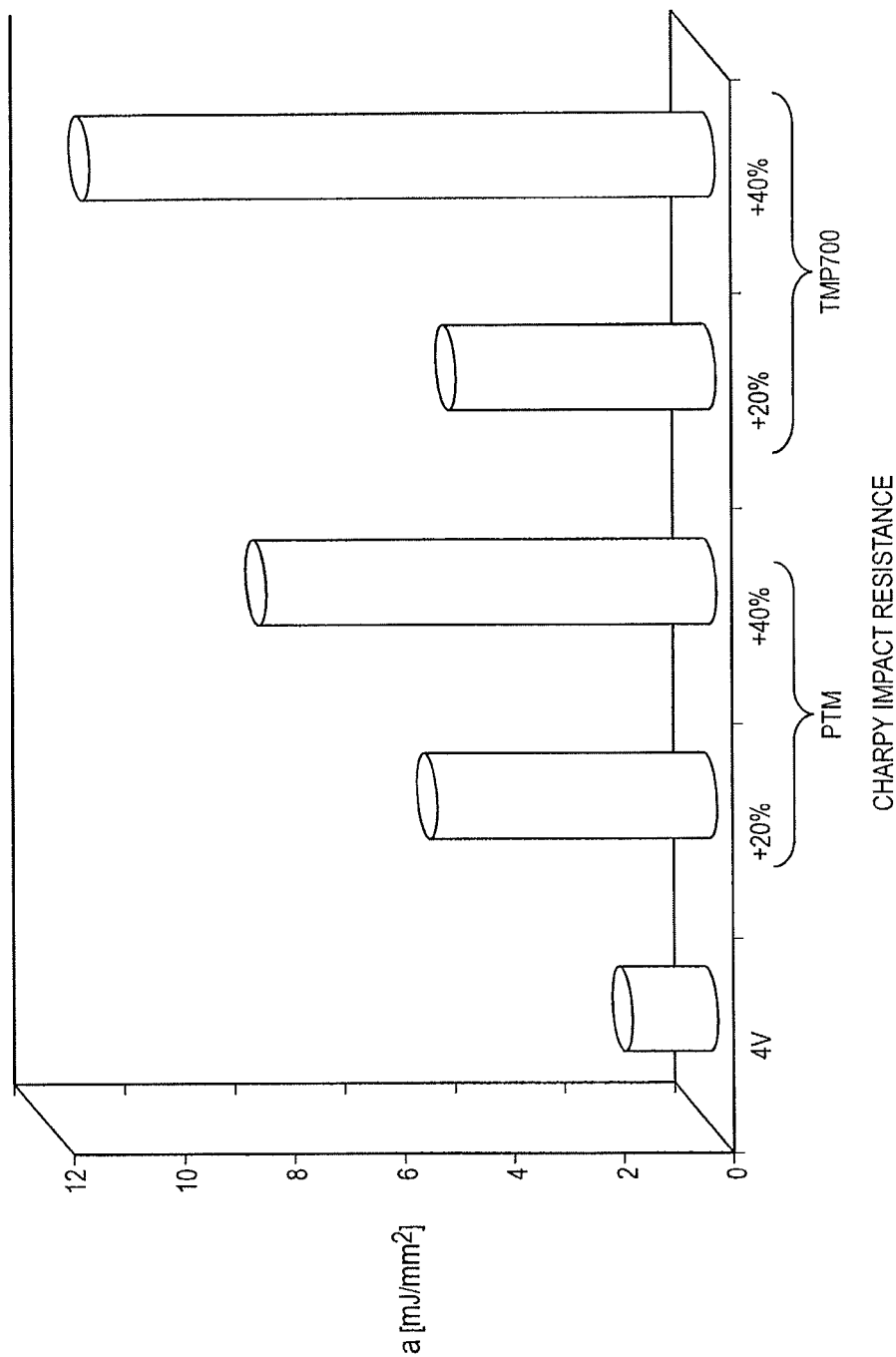
FIG. 8 illustrates Charpy impact resistance of the vinyl ester 4V in presence of various amounts of PTM and TMP700.

The reactivity towards photopolymerization was tested with the help of photo-DSC (differential scanning calorimetry). The measurements were carried out using 2 wt % of 2-hydroxy-1-[4-(2-hydroxyethoxy)phenyl]-2-methyl-1-propanone (Irgacure 2959, Ciba SC) as photoinitiator. The vinyl esters and the references were sorted in 3 groups of similar size and molecular weight and compared within these groups; AVE was compared to 4Ac and 4MA, TUVE and PEG250DVE to TTEGDAc and TTEGDMA, and PEG600DVE to PEG600DAc and PEG600DMA. The results of the photo-DSC measurements of TUVE, PEG250DVE, TTEGDAc, and TTEGDMA containing different amounts of the thiol PTM are shown in Table 9 below and FIGS. 1-4.

TABLE 9

Time To Maximum Polymerization Heat($t_{max}$) of various combinations of monomers and thiols

| $t_{max}$[S] | Fraction Thiol (based on functional groups) | | | |
|---|---|---|---|---|
| Monomer + Thiol | 0 % | 10 % | 20 % | 40 % |
| 4Ac + PTM | 2.7 | 2.5 | 2.8 | 2.7 |
| 4MA + PTM | 28.6 | 87.6 | 83.8 | 55.0 |
| AVE + PTM | 4.9 | 7.7 | 5.8 | 2.1 |
| 4Ac + TMP700 | 2.7 | 2.9 | 3.5 | 3.5 |
| 4MA + TMP700 | 28.6 | 90.2 | 85.4 | 75.0 |
| AVE + TMP700 | 4.9 | 8.4 | 2.9 | 2.1 |
| TTEGDAc + PTM | 2.6 | 3.5 | 3.3 | 3.3 |
| TTEGDMA + PTM | 12.6 | 51.5 | 58.3 | 54.0 |

TABLE 9-continued

Time To Maximum Polymerization Heat($t_{max}$) of various combinations of monomers and thiols

| $t_{max}$[S] | Fraction Thiol (based on functional groups) | | | |
|---|---|---|---|---|
| Monomer + Thiol | 0 % | 10 % | 20 % | 40 % |
| TUVE + PTM | 33.7 | 17.6 | 11.3 | 10.6 |
| PEG250DVE + PTM | 36.7 | 17.2 | 14.4 | 11.9 |
| PEG6000DAc + PTM | 3.2 | 3.2 | 3.0 | 3.0 |
| PEG6000DMA + PTM | 10.5 | 26.3 | 31.2 | 24.9 |
| PEG6000DVE + PTM | 44.4 | 35.0 | 22.9 | 19.9 |

While for acrylates there is no significant difference in the time until the maximum of the polymerization heat ($t_{max}$) is reached, for methacrylates, the polymerization is significantly delayed. In the case of vinyl esters, the peak becomes higher and the slope is much steeper leading to much shorter $t_{max}$, i.e. the reactivity is boosted enormously.

Example 10

Effects of the Monomers 4V, 4M, 4A, and PTM osteoblastic MC3T3-E1 Cells In Vitro

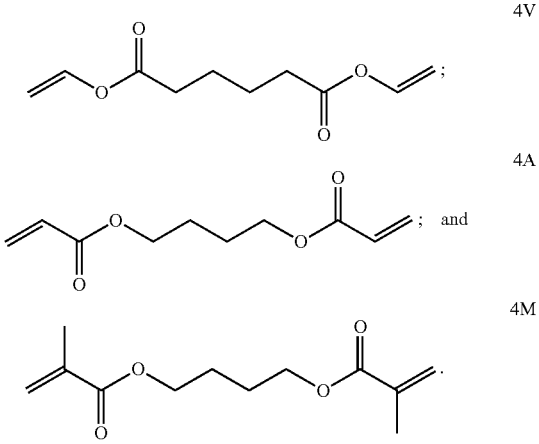

The effects of each of vinyl ester 4V, acrylate 4A, and meth-acrylate 4M on osteoblastic MC3T3-E1 cells in vitro was tested by the MTT assay method. The osteoblastic MC3T3-E1 cells were cultured for five days in the presence of each of vinyl ester (4V), acrylate (4A), and meth-acrylate (4M). The $LC_{50}$ (lethal concentration, 50%) values observed for the monomers are listed in Table 10 below.

TABLE 10

$LC_{50}$ values for vinyl ester 4V, acrylate 4A, and meth-acrylate 4M

| Monomer | $LC_{50}$ [mM] |
|---|---|
| 4V | 6.4 |
| 4M | 1.3 |
| 4A | <0.16 |
| PTM | >10 |

Cytotoxicity of the newly synthesized monomers and the reference substances together with the thiols and photoinitiator used was examined in osteoblast cell culture by using an Alamar Blue Assay. This assay incorporates a fluoromet-ric/colormetric growth indicator based on the detection of metabolic activity.

1M solutions of the monomers, thiols, and photoinitiator in DMSO (HYBRI-MAX®, Sigma) were prepared. Each solution was diluted with Dulbeccos Modified Eagles Medium (DMEM; Sigma), 10% Fetal calf serum (FCS; PAA), 100 U/ml Penicillin (Invitrogen), and 100 μg/ml *Streptomycin* (Invitrogen), to acquire solutions with 7 different concentrations of the monomers (10 mM, 5 mM, 2.5 mM, 1.25 mM, 0.63 mM, 0.31 mM, and 0.16 mM).

For experiments, cells [osteoblasts taken of the strain C57BL/6 of mus musculus (ATCC Catalog No. CRL-2593, MC3T3-E1, Subclone 4)] were cultured in 100 μg/ml DMEM Medium supplemented with 10% FCS, 100 U/ml Penicillin, and 100 μg/ml *Streptomycin*, in 96-well plates at a density of $6.4 \times 10^3$ cells well$^{-1}$ for 24 hours in humidified air (95% relative humidity) with 5% $CO_2$ at 37° C. The next day, the cells were treated with 100 μL of the different concentrations of the monomers for 5 days in triplicates. 10 μL of resazurin were added and the cells incubated for 4 hours at 37° C. The fluorescence intensity was measured for excitation at 530 nm and emission at 580 nm and compared to untreated cells (cells+medium). As control groups cells treated with 1% DMSO-solution, a blank value, and PBS-puffer were used. The results, shown in Table 10 above, represent the mean with standard deviations of triplicate assays (n=3).

Compositions of the present invention are suitable for production of 3D objects, including polymer-based computer-modeled geometrical implants. Accordingly, an aspect of the present invention provides a method of manufacturing a three-dimensional article through an additive manufacturing process such as micro-stereo lithography ("MSL"). The MSL technique can be used to build a 3D object through a process in which the object is formed incrementally through light initiated polymerization of successive layers of the curable composition. Thus, each layer of the 3D structure is formed from a liquid curable composition that solidifies upon exposure to electromagnetic radiation such ultraviolet (UV) light. Because the 3D structures are produced layer by layer, it possible to manufacture patient specific/custom implants in small series expediently and economically.

Accordingly, in an embodiment, the present invention provides a method fabricating a 3D object/structure, which method comprises (a) depositing a layer of a curable composition into a mold of the 3D object/structure; (b) directing an energy (e.g., an electromagnetic radiation) to cause radical polymerization of the curable composition to thereby form a cross-section layer of the 3D object/article, the cross-section layer having a thickness ranging from 0.001 mm to 3 mm, for example 0.03 mm; and (c) repeating steps (a) and (b) to form the three-dimensional article in a layer-wise fashion.

In another embodiment, the method of manufacturing the 3D article in accordance with the present invention includes the steps of (a) illustrating a three-dimensional CAD model of a target 3D article by a 3D CAD system and (b) communicating the illustrated information to a 3D printing system via a computer.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

It should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure herein, processes, machines, manufacture, composition of matter, means, methods, or steps, presently existing or later to be developed that perform substantially the same function or achieve substantially the same result as the corresponding embodiments described herein may be utilized according to the present invention.

The invention claimed is:

1. A curable composition comprising:
   (a) 60 wt. % to 95 wt. % of one or more vinyl ester monomers, wherein said one or more vinyl ester monomers are selected from: (i) a vinyl ester monomer having a formula of

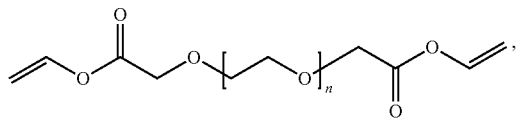

wherein n is an integer from 1 to 12; (ii) monomers selected from diethylene glycol bis[O—(O'-vinylmaleinoyl)-polylactate]) (DVMPL); ω,ω'-3,6,9-trioxaundecanedioic acid divinyl ester (TUVE); polyglutamic acid; polyaspartic acid; hyaluronic acid; polylactic acid; polyglycolic acid; and poly(lactide-co-glycolide); (iii) or combinations thereof;

(b) 0.1 to 40 wt. % of one or more multifunctional thiols selected from the group consisting of ethoxylated pentaerythritol tetra-(3-mercaptopropionate); trimethylpropane tri(3-mercapto-propionate); ethoxylated trimethylpropane tri(3-mercapto-propionate); glycol dimercaptoacetate; trimethylolpropane trimercaptoacetate; pentaerythritol tetramercaptoacetate; ethoxylated trimethylolpropane tri-3-mercaptopropionate; and ethoxylated trimethylolpropane tri-3-mercaptopropionate; polypropylene glycol (3-mercaptopropionate); polypropylene glycol (3-mercaptopropionate);

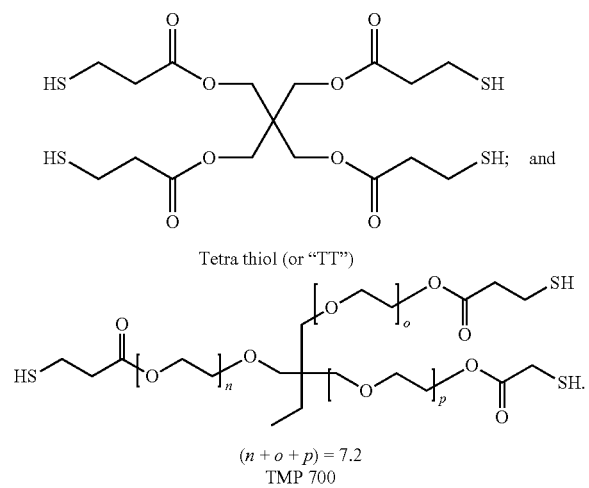

and (c) 0 to 10 wt. % of a biocompatible polymerization initiator.

2. The curable composition according to claim 1, wherein at least one of the vinyl ester monomers accounts for 50 mole percent of all monomers contained.

3. The curable composition of claim 1, wherein said one or more vinyl ester monomers are selected from the group consisting of:

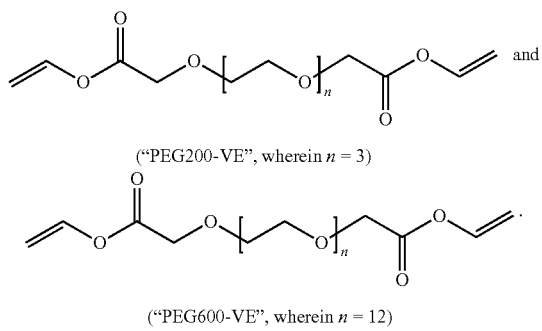

("PEG200-VE", wherein $n = 3$)

("PEG600-VE", wherein $n = 12$)

4. A method for augmenting or filling a structure in a patient comprising,
(a) implanting a curable composition into said patient at a site of the structure, wherein the implanting step is performed by injecting the curable composition through a hole in the patient's skin and into a vertebra, the curable composition comprising:
(aa) 60 wt. % to 95 wt. % of one or more vinyl ester monomers, wherein said one or more vinyl ester monomers are selected from compounds of the general formula (I) below:

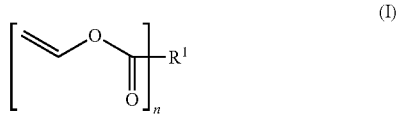

wherein
n independently ranges from 2 to 1000;
$R^1$ is independently selected from the group consisting of:
(i) n-valent radicals, each of said n-valent radicals comprising a carbon chain or a carbon cycle or both, wherein said carbon chain and/or carbon cycle each, independently from one another, comprises from 1 to 30 carbon atoms,
wherein said carbon chain can be straight, branched, saturated or unsaturated, and containing one or more interspersed heteroatoms, said heteroatoms being selected from the group consisting of oxygen, sulfur and nitrogen, and
wherein said carbon chain optionally being substituted with one or more substituents selected from the group consisting of —OH, —COOH, —CN, —CHO, and =O,
wherein said carbon cycle can be saturated or unsaturated, and containing one or more interspersed heteroatoms, said heteroatoms being selected from the group consisting of oxygen, sulfur and nitrogen, and
wherein said carbon cycle optionally being substituted with one or more substituents selected from the group consisting of —OH, —COOH, —CN, —CHO, and =O, and (ii) n-valent radicals of biodegradable, biocompatible oligomers and polymers, said oligomers and polymers being selected from the group consisting of polysaccharides, polypeptides, polyamides, polyesters, polycarbonates, polyethers, and fatty acid derivatives;
(bb) 0.1 to 40 wt. % of one or more multifunctional thiols; and
(cc) 0 to 10 wt. % of a biocompatible polymerization initiator;
(b) initiating said composition to thereby form a resorbable, biocompatible polymer.

5. The method of claim 4, wherein said initiating is performed by irradiating said curable composition.

6. The method of claim 5, wherein said irradiating is performed using an optical fiber inserted at the site of the structure.

7. The method of claim 5, wherein the implanting step has the additional steps of:
inserting a balloon through the hole in the patient's skin into the vertebra;
inflating the balloon to create a void at the site of the structure.

8. The method of claim 4, wherein the structure is located at a site of one or more of the following: a fracture, a deformity, a void, and a tumor.

9. A biodegradable implant comprising: a copolymer having monomer units of:
(a) 60 wt. % to 95 wt. % of one or more vinyl ester monomers wherein said one or more vinyl ester monomers are selected from: (i) a vinyl ester monomer having a formula of

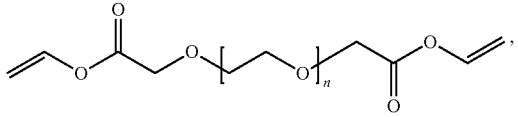

wherein n is an integer from 1 to 12; and (ii) monomers selected from diethylene glycol bis[O—(O'-vinylmaleinoyl)-polylactate]) (DVMPL); ω,ω'-3,6,9-trioxaundecanedioic acid divinyl ester (TUVE); polyglutamic acid; polyaspartic acid; hyaluronic acid; polylactic acid; polyglycolic acid; and poly(lactide-co-glycolide); (iii) or combinations thereof; and
(b) 0.1 to 40 wt. % of one or more multifunctional thiols selected from the group consisting of ethoxylated pentaerythritol tetra-(3-mercaptopropionate); trimethylpropane tri(3-mercapto-propionate); ethoxylated trimethylpropane tri(3-mercapto-propionate); glycol dimercaptoacetate; trimethylolpropane trimercaptoacetate; pentaerythritol tetramercaptoacetate; ethoxylated trimethylolpropane tri-3-mercaptopropionate; and ethoxylated trimethylolpropane tri-3-mercaptopropionate; polypropylene glycol (3-mercaptopropionate); polypropylene glycol (3-mercaptopropionate);

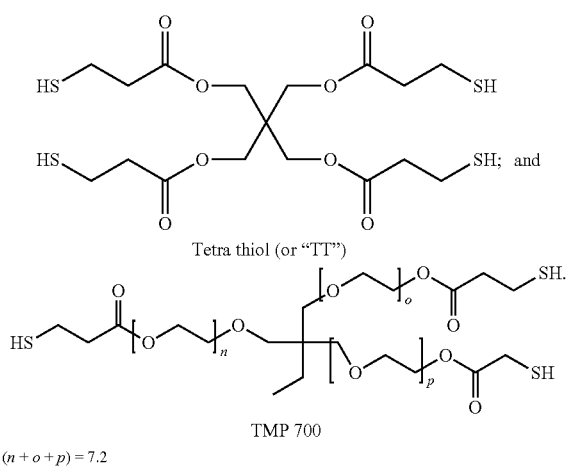

Tetra thiol (or "TT")

TMP 700

(n + o + p) = 7.2

10. A method of manufacturing a three-dimensional article through an additive manufacturing process, said method comprising:
(a) depositing a layer of a curable composition into a mold of three-dimensional article;
(b) directing an energy source to cause radical polymerization of the curable composition to thereby form a cross-section layer of the 3D object/article, the cross-section layer having a thickness ranging from about 0.001 mm to about 3 mm; and
(c) repeating steps (a) and (b) to form the three-dimensional article in a layerwise fashion, wherein the curable composition comprises:
(aa) 60 wt. % to 95 wt. % of one or more vinyl ester monomers, wherein said one or more vinyl ester monomers are selected from: (i) a vinyl ester monomer having a formula of

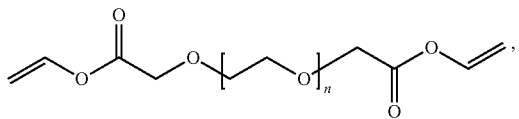

wherein n is an integer from 1 to 12; and (ii) monomers selected from diethylene glycol bis[O—(O'-vinylmaleinoyl)-polylactate]) (DVMPL); ω,ω'-3,6,9-trioxaundecanedioic acid divinyl ester (TUVE); polyglutamic acid; polyaspartic acid; hyaluronic acid; polylactic acid; polyglycolic acid; and poly(lactide-co-glycolide); (iii) or combinations thereof;

(bb) 0.1 to 40 wt. % of one or more multifunctional thiols; and
(cc) 0 to 10 wt. % of a biocompatible polymerization initiator.

11. The curable composition according to claim 1 further comprising one or more additives selected from polymerization sensitizers and inhibitors, stabilizers, modifying agents, softeners, dyeing agents, bioactive agents, cells, thickening agents, and fillers.

12. A method for augmenting or filling a structure in a patient comprising,
(a) implanting a curable composition into said patient at a site of the structure, wherein the implanting step is performed by injecting the curable composition into the patient's oral and maxillofacial region, the curable composition comprising:
(aa) 60 wt. % to 95 wt. % of one or more vinyl ester monomers, wherein said one or more vinyl ester monomers are selected from: (i) a vinyl ester monomer having a formula of

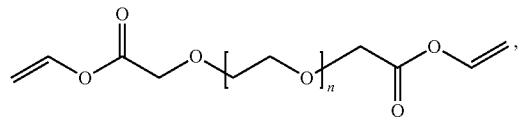

wherein n is an integer from 1 to 12; and (ii) monomers selected from diethylene glycol bis[O—(O'-vinylmaleinoyl)-polylactate]) (DVMPL); ω,ω'-3,6,9-trioxaundecanedioic acid divinyl ester (TUVE); polyglutamic acid; polyaspartic acid; hyaluronic acid; polylactic acid; polyglycolic acid; and poly(lactide-co-glycolide); (iii) or combinations thereof;
(bb) 0.1 to 40 wt. % of one or more multifunctional thiols; and
(cc) 0 to 10 wt. % of a biocompatible polymerization initiator;
(b) initiating said composition to thereby form a resorbable, biocompatible polymer.

13. The method of claim 12, wherein said initiating is performed by irradiating said curable composition.

14. The method of claim 12, wherein said irradiating is performed using an optical fiber inserted at the site of the structure.

15. The method of claim 12, wherein the structure is located at a site of one or more of the following: a fracture, a deformity, a void, and a tumor.

* * * * *